US009023800B2

(12) United States Patent
Offen et al.

(10) Patent No.: US 9,023,800 B2
(45) Date of Patent: *May 5, 2015

(54) PEPTIDES FOR THE TREATMENT OF OXIDATIVE STRESS RELATED DISORDERS

(75) Inventors: Daniel Offen, Kfar HaRoe (IL); Nirit Lev, Ramat-Gan (IL); Eldad Melamed, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/452,986

(22) Filed: Apr. 23, 2012

(65) Prior Publication Data

US 2012/0225822 A1 Sep. 6, 2012

Related U.S. Application Data

(63) Continuation of application No. 13/127,494, filed as application No. PCT/IL2010/000760 on Sep. 16, 2010, now Pat. No. 8,212,001.

(60) Provisional application No. 61/272,367, filed on Sep. 17, 2009.

(51) Int. Cl.
| | |
|---|---|
| A61K 38/00 | (2006.01) |
| A61K 38/04 | (2006.01) |
| A01N 61/00 | (2006.01) |
| A01N 37/18 | (2006.01) |
| C07K 14/47 | (2006.01) |

(52) U.S. Cl.
CPC ............ *C07K 14/4702* (2013.01); *A61K 38/00* (2013.01)

(58) Field of Classification Search
None
See application file for complete search history.

(56) References Cited

U.S. PATENT DOCUMENTS

| 7,211,255 | B2 | 5/2007 | Klinefelte |
| 2005/0069536 | A1 | 3/2005 | Klinefelter |
| 2006/0153807 | A1 | 7/2006 | Abeliovich et al. |
| 2010/0093600 | A1 | 4/2010 | Lev et al. |
| 2011/0212896 | A1 | 9/2011 | Offen et al. |
| 2013/0123187 | A1 | 5/2013 | Lev et al. |

FOREIGN PATENT DOCUMENTS

| WO | WO 2007/095530 | 8/2007 |
| WO | WO 2007/119237 | 10/2007 |
| WO | WO 2008/111063 | 9/2008 |

OTHER PUBLICATIONS

Communication Relating to the Results of the Partial International Search Dated Jul. 28, 2008 From the International Searching Authority Re.: Application No. PCT/IL2008/000336.
International Preliminary Report on Patentability Dated Sep. 24, 2009 From the International Bureau of WIPO Re.: Application No. PCT/IL2008/000336.
International Preliminary Report on Patentability Dated Mar. 29, 2012 From the International Bureau of WIPO Re. Application No. PCT/IL2010/000760.
International Search Report and the Written Opinion Dated Jan. 7, 2011 From the International Searching Authority Re. Application No. PCT/IL2010/000760.
International Search Report Dated Oct. 1, 2008 From the International Searching Authority Re.: Application No. PCT/IL2008/000336.
Official Action Dated Feb. 14, 2012 From the US Patent and Trademark Office Re. U.S. Appl. No. 12/450,076.
Official Action Dated Oct. 21, 2011 From the US Patent and Trademark Office Re. U.S. Appl. No. 13/127,494.
Written Opinion Dated Oct. 1, 2008 From the International Searching Authority Re.: Application No. PCT/IL2008/000336.
Chen et al. "Synaptophysin Enhances the Neuroprotection of VMAT2 in MPP+-Induced Toxicity in MN9D Cells", Neurobiology of Disease, XP004977685, 19(3): 419-426, Aug. 1, 2005.
Mitsumoto et al. "DJ-1 is an Indicator for Endogenous Reactive Oxygen Species Elicited by Endotoxin", Free Radical Research, XP002989099, 35(6): 885-893, Dec. 1, 2001.
Pan et al. "Biological Effects of Pramipexole on Dopaminergic Neuron-Associated Genes: Relevance to Neuroprotection", Neuroscience Letters, XP004766570, 377(2): 106-109, Mar. 29, 2005.
Sievert et al. "High-Efficiency Expression and Characterization of the Synaptic-Vesicle Monoamine Transporter From Baculovirus-Infected Insect Cells", Biochemistry Journal, 330: 959-966, 1998.
Clements et al. "DJ-1, A Cancer- and Parkinson's Disease-Associated Protein, Stabilizes the Antioxidant Transcriptional Master Regulator Nrf2", Proc. Natl. Acad. Sci. USA, PNAS, 103(41): 15091-15096, Oct. 10, 2006.
ProHealth "Dopamine-Preserving Peptide Stops Parkinson's Nerve Damage in Preclinical Trials", ProHealth Inc., 2 P., May 3, 2012.
Translation of Office Action Notice Dated Jul. 10, 2013 From the State Intellectual Property Office of the People's Republic of China Re. Application No. 201080041696.2.
Translation of Search Report Notice Dated Jul. 10, 2013 From the State Intellectual Property Office of the People's Republic of China Re. Application No. 201080041696.2.
Official Action Dated Sep. 25, 2013 From the US Patent and Trademark Office Re. U.S. Appl. No. 13/662,697.
Taira et al. "Molecular Cloning of Human and Mouse DJ-1 Genes and Identification of Sp1-Dependent Activation of the Human DJ-1 Promoter", Gene, 263(1-2): 285-292, 2001.
Official Action Dated Apr. 4, 2014 From the US Patent and Trademark Office Re. U.S. Appl. No. 13/662,697.
Larsen et al. "DJ-1 Protein [Sus Scrofa]", NCBI GenBank Database [Online], GenBank Version AAY56774.1, GenBank Accession No. AAY56774, Feb. 12, 2007.
Larsen et al. "Porcine DJ-1: Cloning of PARK7 cDNA, Sequence Comparison, Expression Analysis and Chromosomal Localization", Cytogenetic and Genome Research, 116(1-2): 93-99, 2007.
Larsen et al. "Sus Scrofa DJ-1 Protein (PARK7) Gene, Exon 2 and Partial CDS", NCBI GenBank Database [Online], GenBank Version DQ008987.1, GenBank Accession No. DQ008987, Feb. 12, 2007.

(Continued)

*Primary Examiner* — Olga N Chernyshev

(57) ABSTRACT

Isolated DJ-1 related peptides are disclosed and pharmaceutical compositions comprising same for treating oxidative stress-related disorder.

2 Claims, 19 Drawing Sheets
(1 of 19 Drawing Sheet(s) Filed in Color)

(56) References Cited

OTHER PUBLICATIONS

Communication Pursuant to Article 94(3) EPC Dated Mar. 18, 2014 From the European Patent Office Re. Application No. 10768079.5.

Jones et al. "Characterisation of Cell-Penetrating Peptide-Mediated Peptide Delivery", British Journal of Pharmacology, XP002566101, 145: 1093-1102, 2005.
Lindsay "Peptide-Mediated Cell Delivery: Application in Protein Target Validation", Current Opinion in Pharmacology, XP008041390, 2: 587-594, 2002.

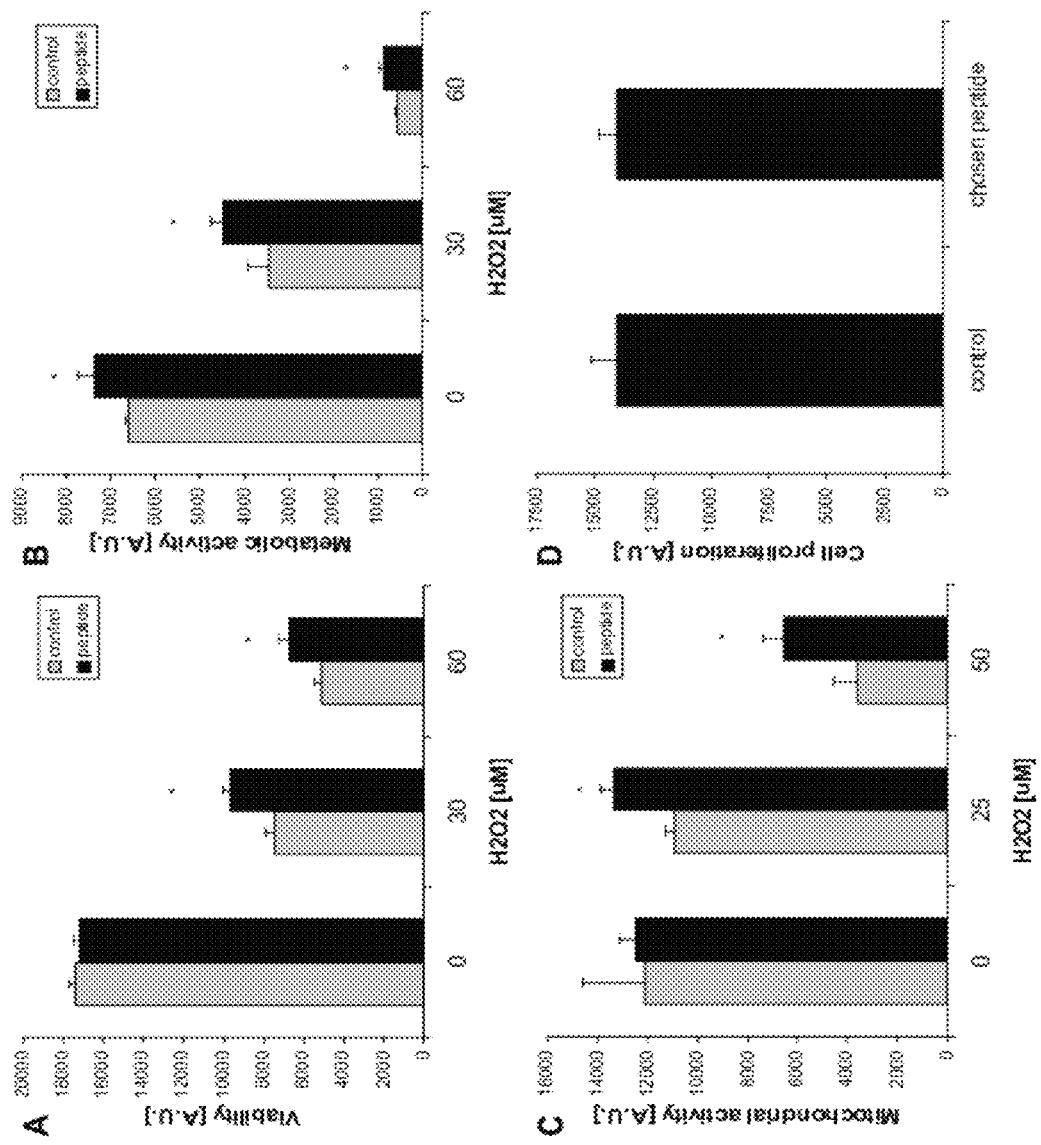
FIGs. 1A-D

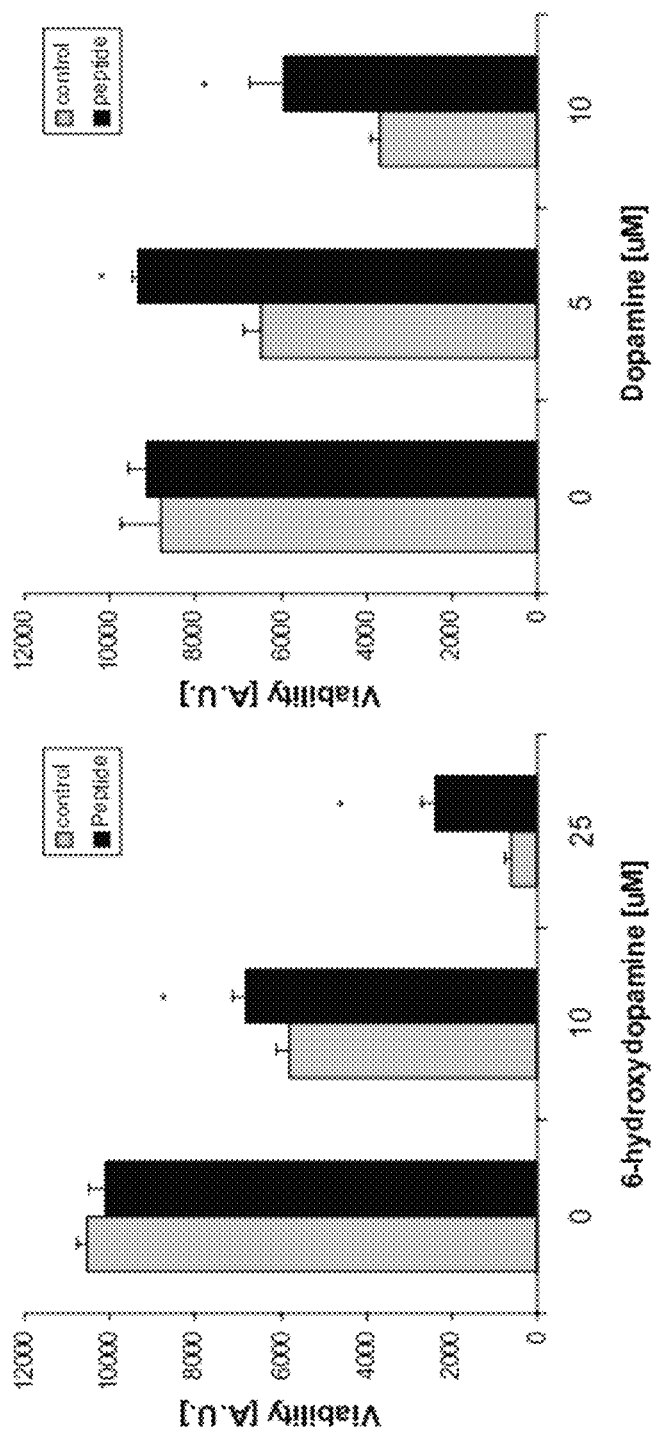

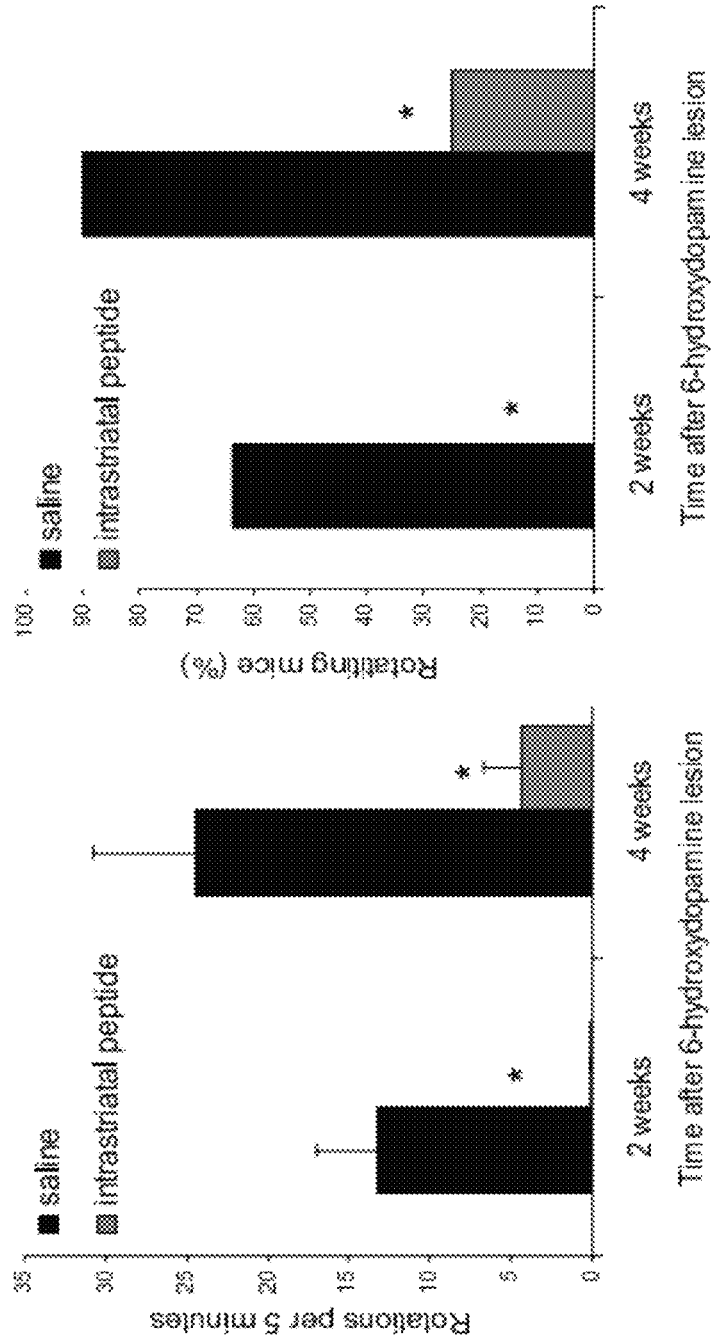

PEPTIDES FOR THE TREATMENT OF OXIDATIVE STRESS RELATED DISORDERS

RELATED APPLICATIONS

This application is a continuation of U.S. patent application Ser. No. 13/127,494 filed on May 4, 2011, which is a National Phase of PCT Patent Application No. PCT/IL2010/000760 having International filing date of Sep. 16, 2010, which claims the benefit of priority of U.S. Provisional Patent Application No. 61/272,367 filed on Sep. 17, 2009. The contents of the above applications are all incorporated herein by reference.

FIELD AND BACKGROUND OF THE INVENTION

The present invention, in some embodiments thereof, relates to peptide agents for the treatment of oxidative stress related disorders.

Free radicals are extremely reactive chemical species that cause significant destruction in biological systems. Indiscriminate reaction of free radicals with biological molecules can lead to the destruction of cells and cellular components (e.g. mitochondria), thereby affecting physiological processes by causing cells to lose their structure and/or function.

In biological systems, free radicals are generally referred to as 'reactive oxygen species' (ROS). ROS are derived from endogenous sources via the metabolism of oxygen containing species, and from exogenous sources such as toxins and atmospheric pollutants.

Attack of ROS on biological molecules is referred to as 'oxidative stress'. Oxidative stress has been implicated as a causative factor in a number of degenerative diseases.

Parkinson's disease (PD) is a multifactorial disease caused by both genetic and environmental factors. Although most patients suffering from PD have a sporadic disease, several genetic causes have been identified in recent years. An increasing number of genes that cause inherited forms of PD have provided the opportunity for new insights into the mechanisms at the basis of the disease. These genes include alpha-synuclein, parkin, PINK1, dardarin (LRRK2), and DJ-1.

Current concepts of the pathogenesis of PD center on the formation of ROS and the onset of oxidative stress leading to oxidative damage to substantia nigra pars compacta. Extensive postmortem studies have provided evidence to support the involvement of oxidative stress in the pathogenesis of PD; in particular, these include alterations in brain iron content, impaired mitochondrial function, alterations in the antioxidant protective systems (most notably superoxide dismutase [SOD] and reduced glutathione [GSH]), and evidence of oxidative damage to lipids, proteins, and DNA. Iron can induce oxidative stress, and intranigral injections have been shown to induce a model of progressive parkinsonism.

Multiple sclerosis (MS) is an inflammatory, demyelinating disease of the central nervous system (CNS), characterized by various symptoms of neurological dysfunction. MS and its animal model, experimental autoimmune encephalomyelitis (EAE), are believed to result from autoimmune mediated activated immune cells such as T- and B-lymphocytes as well as macrophages and microglia. Pathologically, MS is characterized by perivenous infiltration of lymphocytes and macrophages into the CNS parenchyma, resulting in demyelinative lesions termed plaques. These plaques, which are the hallmark of MS, are associated with oligodendrocytes death, axonal damage and neuronal loss. The view that MS can be considered an inflammatory neurodegenerative disease is supported by studies demonstrating neuronal and axonal injury in regions remote from acute plaques, as well as imaging studies that demonstrated changes in normal appearing white and grey matter.

The etiology of MS has not yet been fully elucidated, and it has been attributed to both genetic and environmental causes. Accumulating data indicate that oxidative stress plays a major role in the pathogenesis of MS. Reactive oxygen species (ROS), leading to oxidative stress, generated in excess primarily by activated microglia, have been implicated as mediators of demyelination and axonal damage in both MS and EAE.

The neurotransmitter glutamate is one of the sources of oxidative stress in the MS primarily through activation of its ionotropic receptors. Oligodendrocytes, the myelin-producing cell of the CNS, are also highly vulnerable to glutamate excitotoxicity, mainly via the AMPA/kainate receptors. ROS causes damage to cardinal cellular components such as lipids, proteins and nucleic acids, resulting in cell death. Weakened cellular antioxidant defense systems in the CNS of MS patients resulting in increased vulnerability to ROS effects may increase CNS damage.

Amyotrophic lateral sclerosis (ALS), also called Lou Gehrig's disease, is a progressive, fatal neurological disease affecting as many as 30,000 Americans with 5,000 new cases occurring in the United States each year. The disorder belongs to a class of disorders known as motor neuron diseases. ALS occurs when specific nerve cells in the brain and spinal cord that control voluntary movement gradually degenerate. Familial amyotrophic lateral sclerosis (FALS) is a form of ALS distinguished from the more common sporadic variant only by its familial background.

There is substantial evidence to support the hypothesis that oxidative stress is a contributor to motor neuron death. For example, it has been discovered that mutation of the antioxidant enzyme, superoxide dismutase 1 (SOD1), causes disease in a significant minority of cases.

DJ-1 is a small 189 amino acid protein that is ubiquitously expressed and highly conserved throughout diverse species. Accumulating data revealed its involvement in various cellular processes, especially in oxidative stress. DJ-1 is known to have several isoforms with isoelectric points between 5.5 and 7, with dominance of alkaline isoforms in normal conditions. Upon ROS exposure there is accumulation of more acidic isoforms of DJ-1, mediated through oxidation of cysteine residues [Bandopadhyay R, et al., Brain 127: 420-430, 2004; Canet-Aviles et al., Proc Natl Acad Sci USA 101: 9103-9108, 2004].

DJ-1 is widely distributed and is highly expressed in the brain, and is not confined to a single functional system or anatomical location. DJ-1 is expressed in neurons of different neurotransmitter phenotypes and in all glial cell types, such as astrocytes, microglia and oligodendrocytes. Recently DJ-1 mutations were discovered and associated with familial Parkinson's disease (PD) [Bonifati et al., 2003, Science 299: 256-9, 2003]. A post-mortem study of brain samples from sporadic PD brains versus control found that acidic isoforms of DJ-1 are more abundant in PD brains [Bandopadhyay R, et al., Brain 127: 420-430, 2004]. DJ-1 immunoreactivity was detected in other neurodegenerative diseases including multi-system atrophy, Alzheimer's disease, progressive supra-nuclear palsy, fronto-temporal dementia with parkinsonism linked to chromosome 17, and Pick's disease [Bandopadhyay R, et al., Brain 127: 420-430, 2004; Neumann N. et al., Acta Neuropathol (Berl) 107: 489-496, 2004; Rizzu P. et al., Ann Neurol 55: 113-118, 2004].

WO2007/119237 discusses an analysis of DJ-1 levels and activity for diagnosing oxidative stress related disorders.

U.S. Pat. Appl. No. 20060153807 and U.S. Pat. Appl. No. 20060171935 discusses vector mediated gene regulation of, e.g., DJ-1-associated agents for the treatment of neurodegenerative diseases such as Parkinson's.

WO2008/111063 discusses peptide agents capable of upregulating DJ-1-dependent VMAT2 transcription for the treatment of neurodegenerative diseases.

SUMMARY OF THE INVENTION

According to an aspect of some embodiments of the present invention there is provided an isolated peptide being no longer than 25 amino acids comprising a sequence as set forth in SEQ ID NO: 3, wherein the isolated peptide increases viability of a cell under oxidative stress conditions.

According to an aspect of some embodiments of the present invention there is provided a pharmaceutical composition comprising an isolated peptide, or peptide mimetic thereof, no longer than 25 amino acids comprising at least 2 consecutive amino acids from the amino acid sequence as set forth in SEQ ID NO: 1, and a pharmaceutically acceptable carrier, wherein the isolated peptide increases viability of a cell under oxidative stress conditions.

According to an aspect of some embodiments of the present invention there is provided a pharmaceutical composition comprising an isolated peptide, or peptide mimetic thereof, no longer than 25 amino acids comprising at least 2 consecutive amino acids from the amino acid sequence as set forth in SEQ ID NO: 2, wherein the isolated peptide increases viability of a cell under oxidative stress conditions.

According to an aspect of some embodiments of the present invention there is provided a method of treating an oxidative stress-related disorder in a subject in need thereof, the method comprising administering to the subject a therapeutically effective amount of the pharmaceutical composition of the present invention, thereby treating the oxidative stress-related disorder.

According to an aspect of some embodiments of the present invention there is provided an isolated peptide, or peptide mimetic thereof, no longer than 25 amino acids comprising at least 2 consecutive amino acids from the amino acid sequence as set forth in SEQ ID NO: 1, and a pharmaceutically acceptable carrier, wherein the isolated peptide increases viability of a cell under oxidative stress conditions.

According to an aspect of some embodiments of the present invention there is provided an isolated peptide, or peptide mimetic thereof, no longer than 25 amino acids comprising at least 2 consecutive amino acids from the amino acid sequence as set forth in SEQ ID NO: 2, wherein the isolated peptide increases viability of a cell under oxidative stress conditions.

According to some embodiments of the invention, the isolated peptide comprises a sequence as set forth in SEQ ID NO:3.

According to some embodiments of the invention, the isolated peptide comprises a sequence as set forth in SEQ ID NO:14.

According to some embodiments of the invention, the isolated peptide is as set forth in SEQ ID NO: 24.

According to some embodiments of the invention, the isolated peptide comprises at least 5 consecutive amino acids from the amino acid sequence as set forth in SEQ ID NO: 1.

According to some embodiments of the invention, the isolated peptide comprises at least 5 consecutive amino acids from the amino acid sequence as set forth in SEQ ID NO: 2.

According to some embodiments of the invention, the isolated peptide comprises no more than 15 consecutive amino acids from the amino acid sequence as set forth in SEQ ID NO: 1.

According to some embodiments of the invention, the isolated peptide comprises comprising no more than 15 consecutive amino acids from the amino acid sequence as set forth in SEQ ID NO: 2.

According to some embodiments of the invention, the isolated peptide is no longer than 20 amino acids.

According to some embodiments of the invention, the isolated peptide comprises a sequence as set forth in SEQ ID NO: 38.

According to some embodiments of the invention, the isolated peptide comprises a sequence as set forth in SEQ ID NO: 39.

According to some embodiments of the invention, the isolated peptide comprises a sequence as set forth in SEQ ID NO: 10.

According to some embodiments of the invention, the isolated peptide comprises a sequence as set forth in SEQ ID NO: 11.

According to some embodiments of the invention, the isolated peptide comprises a sequence as set forth in SEQ ID NO: 1 or 3.

According to some embodiments of the invention, the isolated peptide comprises a sequence as set forth in SEQ ID NO: 40.

According to some embodiments of the invention, the isolated peptide comprises a sequence as set forth in SEQ ID NO: 13.

According to some embodiments of the invention, the isolated peptide comprises a sequence as set forth in SEQ ID NO: 41.

According to some embodiments of the invention, the isolated peptide comprises a sequence as set forth in SEQ ID NO: 42.

According to some embodiments of the invention, the isolated peptide comprises a sequence as set forth in SEQ ID NO: 2.

According to some embodiments of the invention, at least one of the amino acids is a naturally occurring amino acid.

According to some embodiments of the invention, at least one of the amino acids is a synthetic amino acid.

According to some embodiments of the invention, the isolated peptide is attached to a cell penetrating agent.

According to some embodiments of the invention, the attached is covalently attached.

According to some embodiments of the invention, the cell penetrating agent is a peptide agent.

According to some embodiments of the invention, the peptide cell penetrating agent comprises an amino acid sequence selected from the group consisting of SEQ ID NOs: 21-23.

According to some embodiments of the invention, the isolated peptide is as set forth in SEQ ID NOs: 24-36.

According to some embodiments of the invention, the cell comprises a neuronal cell.

According to some embodiments of the invention, the ROS conditions are selected from the group consisting of 6-hydroxydopamine toxicity, hydrogen peroxide toxicity, UV radiation and dopamine toxicity.

According to some embodiments of the invention, the oxidative stress-related disorder is a neurodegenerative disease.

According to some embodiments of the invention, the neurodegenerative disease is selected from the group consisting of Parkinson's disease, Multiple Sclerosis, ALS, multi-system atrophy, Alzheimer's disease, stroke, progressive supranuclear palsy, fronto-temporal dementia with parkinsonism linked to chromosome 17 and Pick's disease.

According to some embodiments of the invention, the isolated peptide is for use in treating an oxidative stress-related disorder.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F are bar graphs illustrating that DJ-1-related peptide TAT 2a (SEQ ID NO: 24) is protective in vitro against oxidative and toxic insults. Increased cell viability (A), decreased mitochondrial damage (B) and increased metabolic activity (C) were found with DJ-1-related peptide treatment as compared to saline alone, after exposure to oxidative stress, induced by exposure to $H_2O_2$. Cell proliferation was measured by quantifying [$^3$H]thymidine incorporation. There was no increased cell proliferation with exposure to the peptides (D). Protection against 6-hydroxydopamine and dopamine toxicity are shown in FIGS. 1E and F, respectively. The presented experiments were done on human neuroblastoma SH-SY5Y cells, and repeated at least 3 times. *$p<0.05$, as compared to control cells treated with vehicle and exposed to the same toxic insult.

Figure 2A:
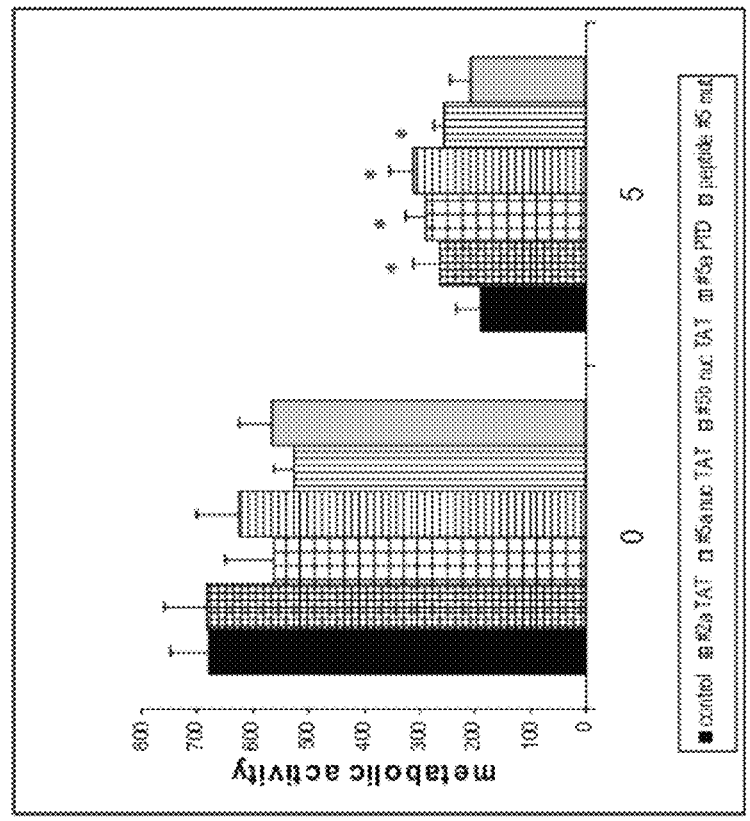
Figure 2B:
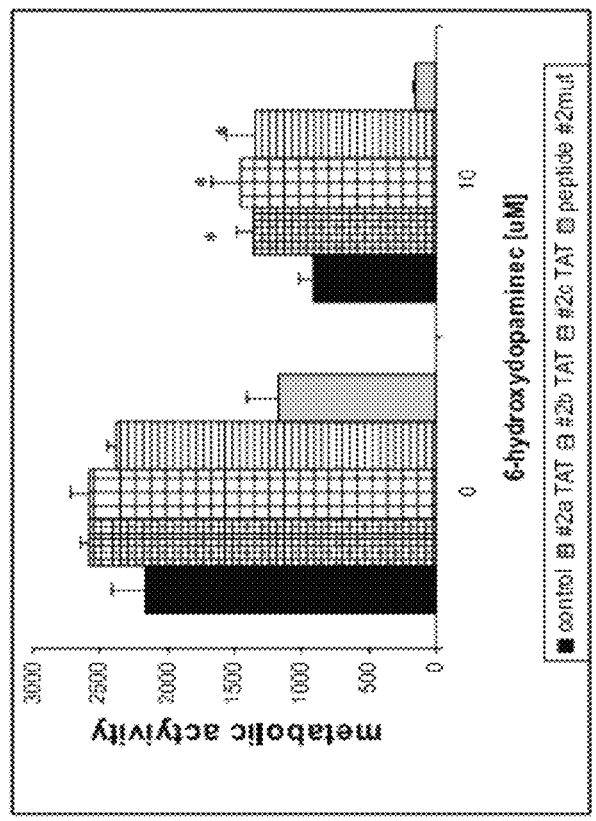

FIGS. 2A-B are bar graphs illustrating that DJ-1-related peptides are protective in vitro against 6-hydroxydopamine toxicity. Increased metabolic activities were found when human neuroblastoma cells SH-SY5Y were pretreated with DJ-1-related peptides as compared to saline before exposure to 6-hydroxydopamine, Protection against 6-hydroxydopamine toxicity by derivatives of DJ-1 related peptide #2 are shown in FIG. 2A and protection against 6-hydroxydopamine toxicity by derivatives of DJ-1 related peptide #5 are shown in FIG. 2B. Mutated peptides failed to protect against 6-hydroxydopamine toxicity as shown in FIGS. 2A-B. The presented experiments were done on human neuroblastoma SH-SY5Y cells, and repeated at least 3 times. *$p<0.05$, as compared to control cells exposed to the same toxic insult.

Figure 3:
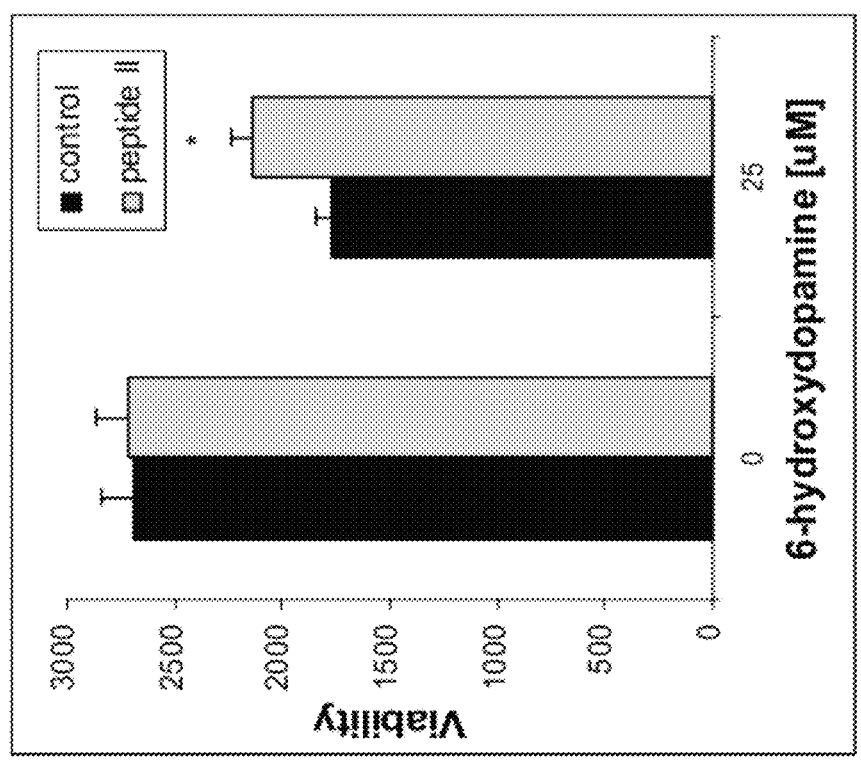

FIG. 3 illustrates that DJ-1-related peptides are protective in vitro against 6-hydroxydopamine toxicity. Increased viability was found when human neuroblastoma cells SH-SY5Y were pretreated with DJ-1-related peptide II (SEQ ID NO: 8) as compared to saline before exposure to 6-hydroxydopamine, *$p<0.05$, as compared to control cells exposed to the same toxic insult.

Figure 4A:
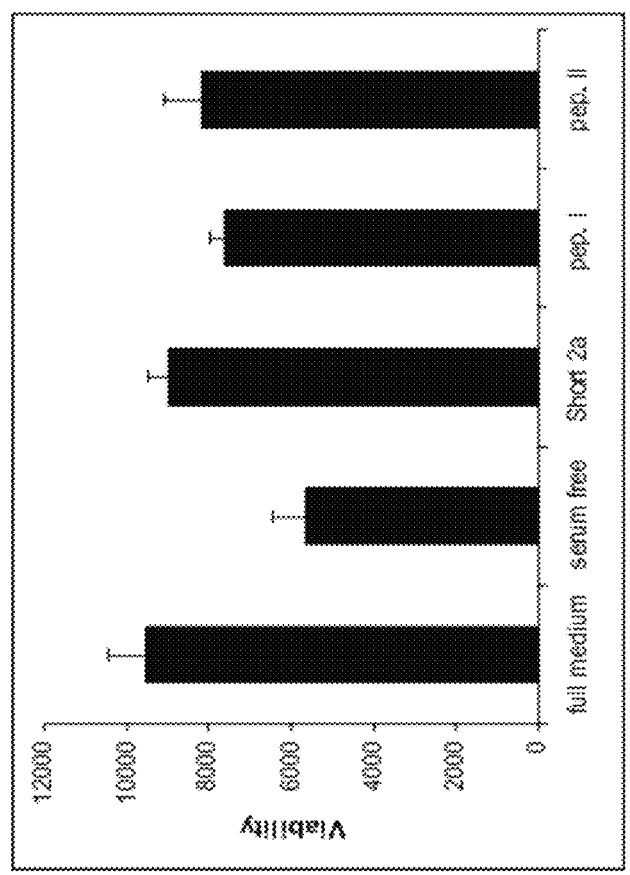

FIG. 4A is a bar graph illustrating that DJ-1-related peptides are protective against serum deprivation. Increased viability was found when human neuroblastoma cells SH-SY5Y were pretreated with DJ-1-related peptide I (SEQ ID NO: 10), II (SEQ ID NO: 8) and short 2a (SEQ ID NO: 9) as compared to saline during serum deprivation, *$p<0.05$.

Figure 4B:
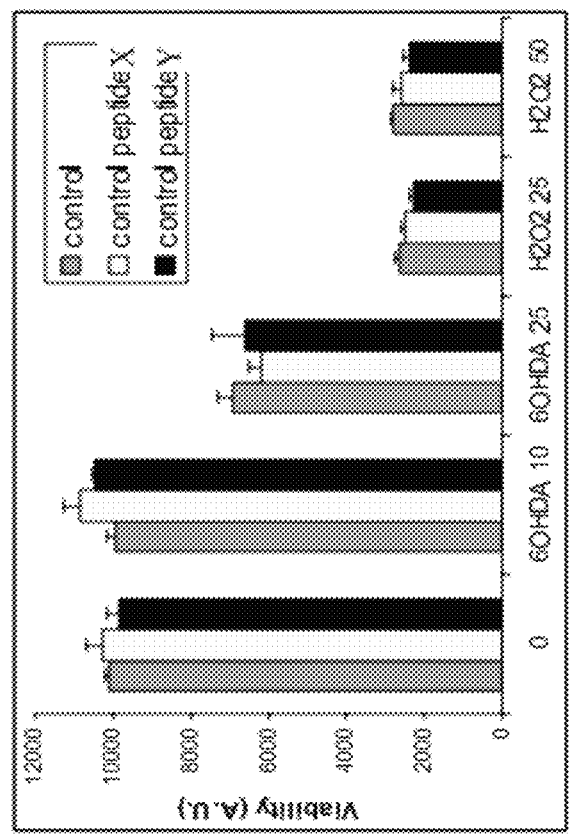

FIG. 4B is a bar graph illustrating that control DJ-1 related peptides are not protective against oxidative and toxin-induced toxicity. Cells were exposed to increasing doses of 6-hydroxydopamine (0-25 uM) or to hydrogen peroxide ($H_2O_2$, 0-50 uM) with or without pretreatment with control peptides X and Y (sequences that were not prospected to induce neuroprotection). The presented experiments were done on human neuroblastoma SH-SY5Y cells, and repeated 3 times. No significant differences were observed compared to control cells treated with vehicle and exposed to the same toxic dose.

Figure 5A:
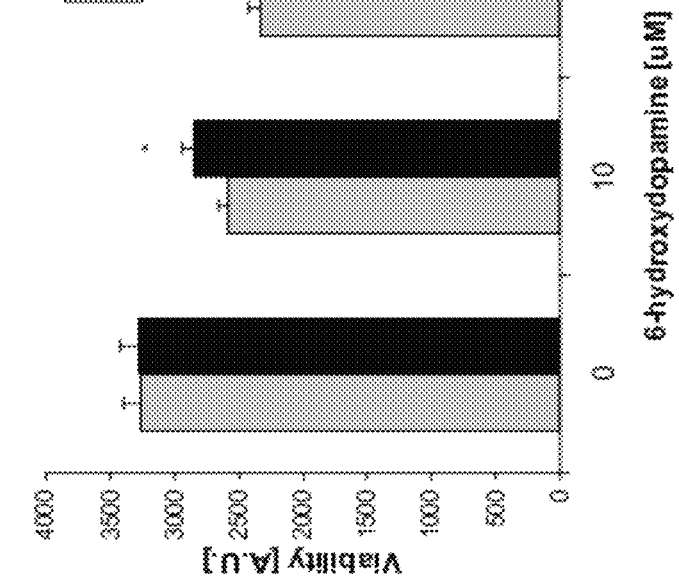
Figure 5B:
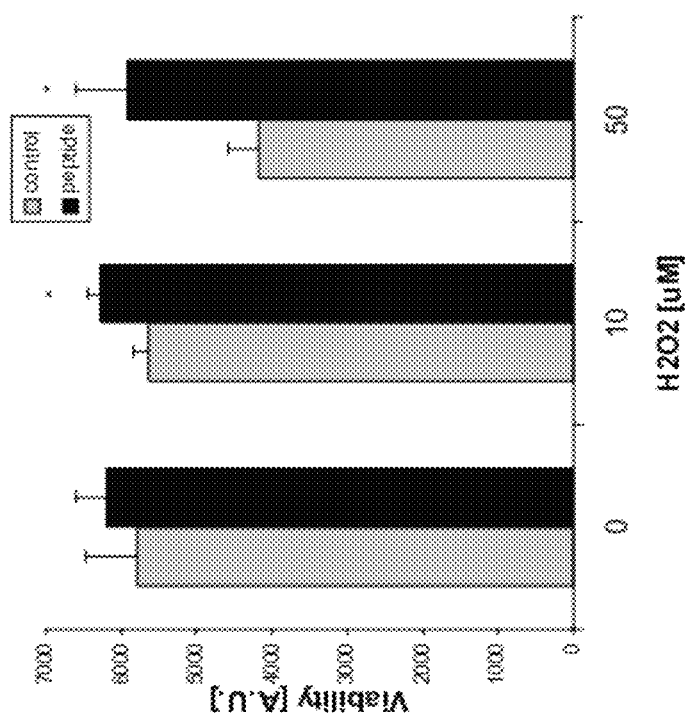

FIGS. 5A-B are bar graphs illustrating protection against $H_2O_2$ and 6-hydroxydopamine toxicity by TAT 2a (SEQ ID NO: 24) peptide in primary cultures. Similar protection against increasing concentrations of hydrogen peroxide and 6-hydroxydopamine was demonstrated in primary mixed neuronal and glial cultures obtained from cortex of postnatal wild type C57/bl mice. Each experiment was repeated for 3 times. *$p<0.05$, as compared to control cells treated with vehicle and exposed to the same toxic insult.

Figure 6:
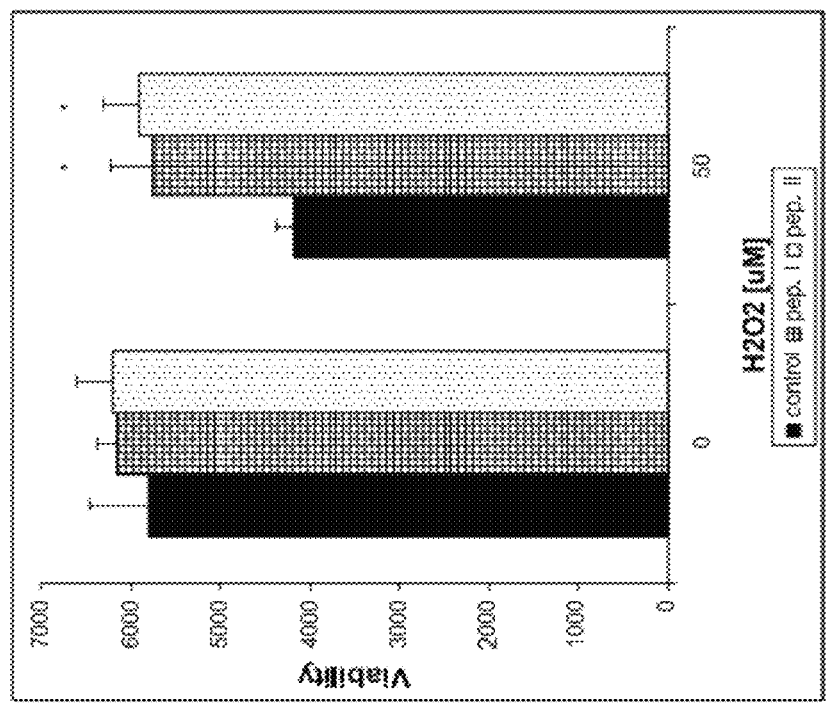

FIG. 6 is a bar graph illustrating DJ-1-related peptides I (SEQ ID NO: 23) and II (SEQ ID NO: 8) are protective against oxidative insult in neuronally differentiated murine neural stem cells. Increased viability was found when these cells were pretreated with DJ-1-related peptide I or II as compared to saline before exposure to hydrogen peroxide ($H_2O_2$), *$p<0.05$, as compared to control cells exposed to the same toxic insult.

Figure 7B:
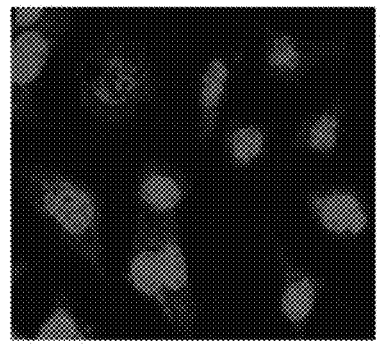
Figure 7A:
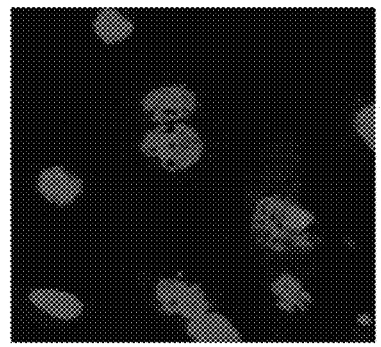

FIGS. 7A-B are photographs illustrating immunohistochemical staining for alpha-synuclein in naïve neuroblastoma cells (FIG. 7A) and cells stably transfected with A53T mutant alpha-synuclein (FIG. 7B). Alpha-synuclein stains red by Alexa-568 conjugated secondary antibodies. Nuclei were counterstained by DAPI (blue). The experiment was repeated 3 times in triplicates.

Figure 8:
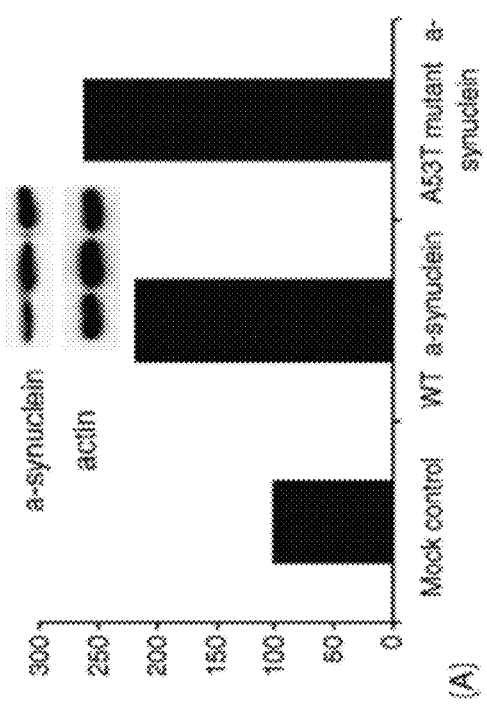

FIG. 8 is a bar graph illustrating graphic quantification of alpha-synuclein and a photograph of a representative Western blot for alpha-synuclein in mock transfected neuroblastoma cells and cells stably transfected with wild type (WT) alpha-synuclein or A53T mutant alpha-synuclein. The experiment was repeated 3 times in triplicates.

Figure 9:
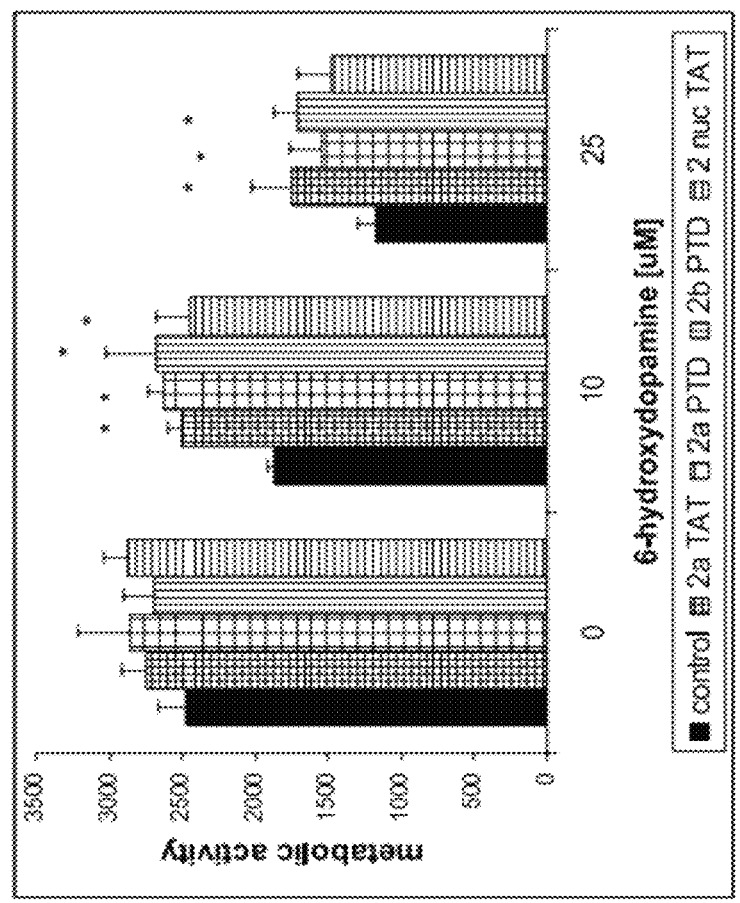

FIG. 9 is a bar graph illustrating protection against 6-hydroxydopamine toxicity by derivatives of peptide #2 in cells overexpressing mutant alpha-synuclein. Significantly increased metabolic activity was demonstrated in neuroblastoma cells overexpressing A53T alpha-synuclein exposed to 6-hydroxydopamine, when treated with derivatives of DJ-1-related peptide #2. Each experiment was repeated for 3 times. *$p<0.05$, as compared to control cells treated with vehicle and exposed to the same toxic insult.

Figure 10:
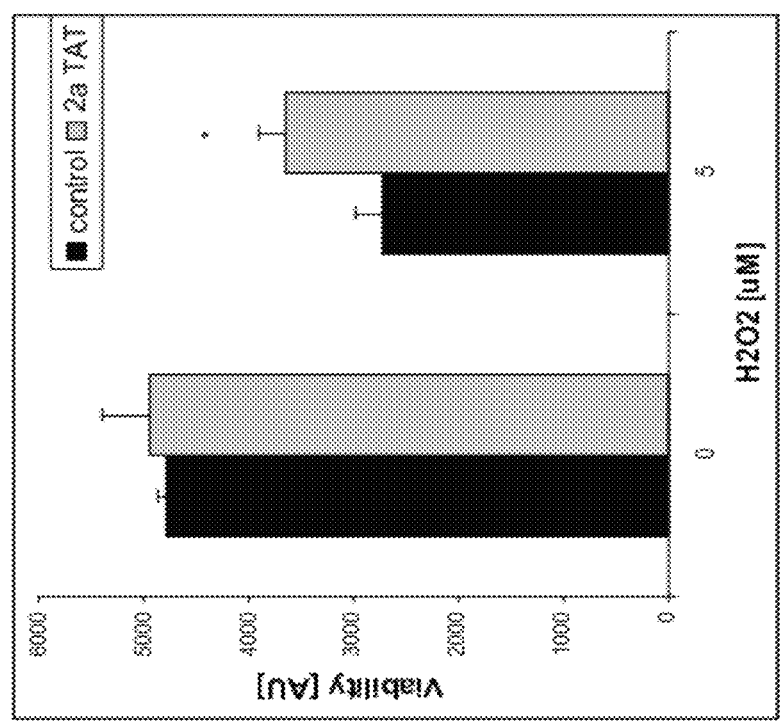

FIG. 10 is a bar graph illustrating protection against hydrogen peroxide toxicity by peptide TAT 2a (SEQ ID NO: 24) in cells overexpressing mutant alpha-synuclein. Significantly increased viability was demonstrated in neuroblastoma cells overexpressing A53T alpha-synuclein exposed to hydrogen peroxide, when treated with DJ-1-related peptide TAT 2a (SEQ ID NO: 24). *$p<0.05$, as compared to control cells treated with vehicle and exposed to the same toxic insult.

Figure 11:
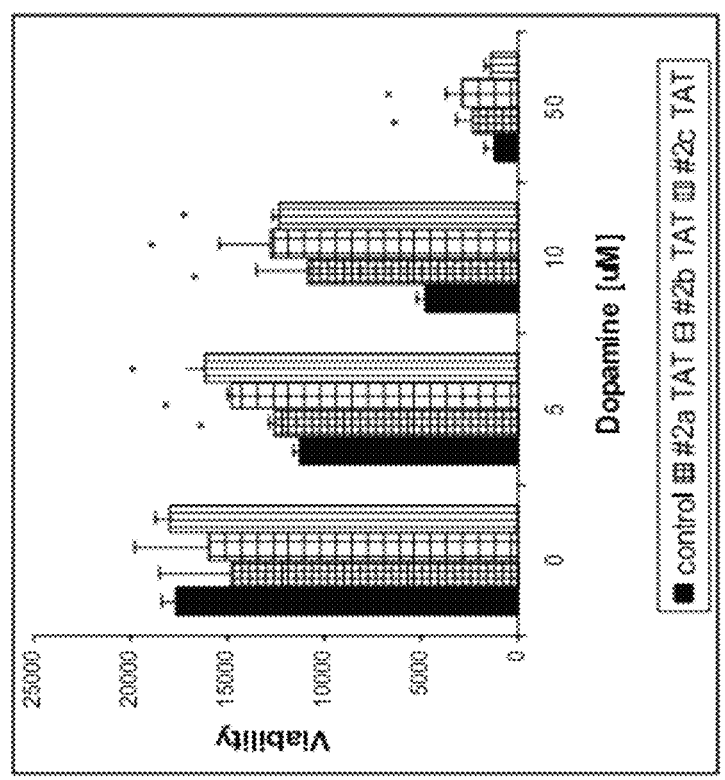

FIG. 11 is a bar graph illustrating that DJ-1-related peptides are protective in vitro against dopamine toxicity. Cells were exposed to increasing doses of dopamine (0-50 uM) with or without pretreatment with derivatives of DJ-1 related peptide #2. The presented experiments were done on human neuroblastoma SH-SY5Y cells, and repeated 3 times. *p<0.05, as compared to control cells treated with vehicle and exposed to the same dopamine dose.

Figure 12A:
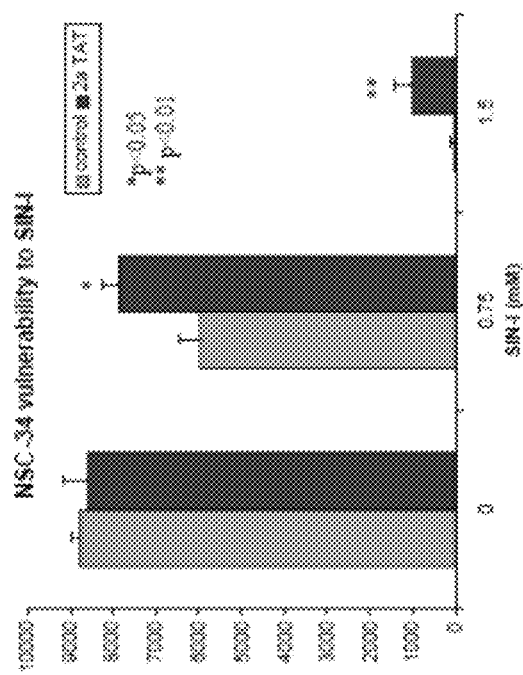
Figure 12B:
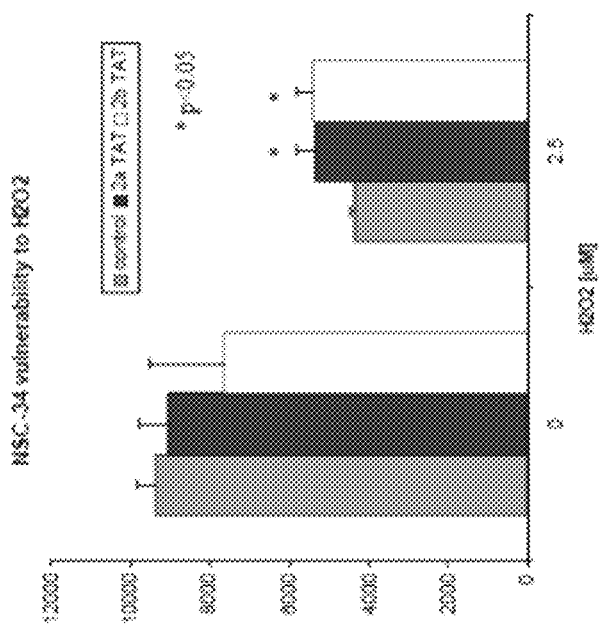

FIGS. 12A-B are bar graphs illustrating that DJ-1-related peptides are protective against hydrogen peroxide and SIN-I toxicity in NSC-34 cells. Increased viability was found when NSC-34 cells were pretreated with DJ-1-related peptides TAT 2a (SEQ ID NO: 24) or TAT 2b (SEQ ID NO: 25) as compared to saline before exposure to hydrogen peroxide (FIG. 12A) or SIN-I (FIG. 12B) toxicity, *p<0.05, **p<0.01 as compared to control cells exposed to the same toxic insult.

Figure 13:
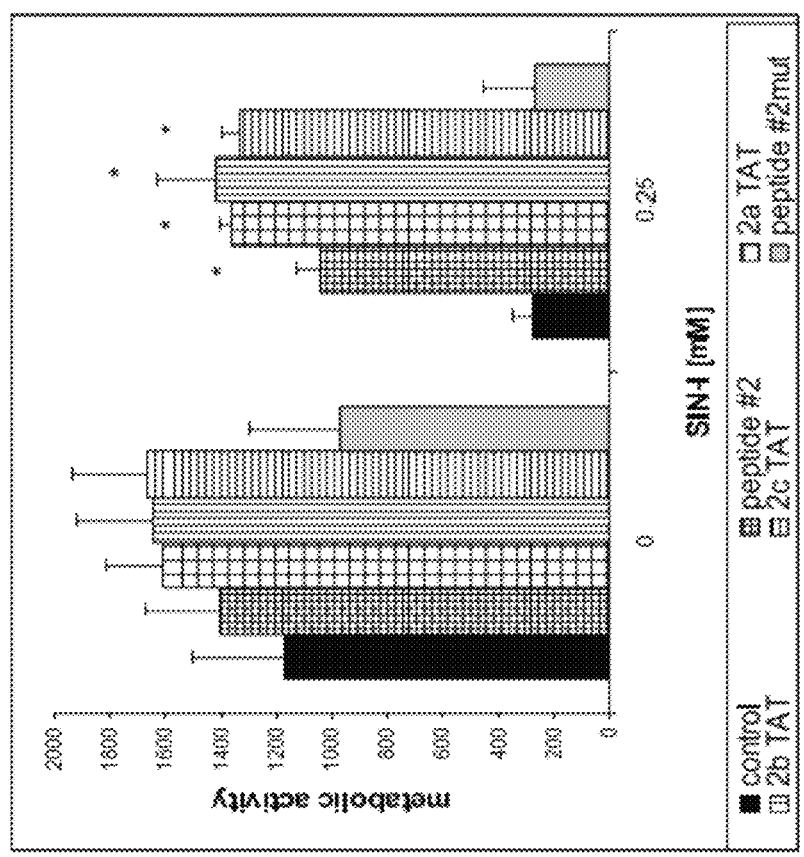

FIG. 13 is a bar graph illustrating that derivatives of DJ-1-related peptide #2 are protective in a cellular model of ALS. Increased metabolic activities were found when NSC-34 cells were pretreated with derivatives of DJ-1-related peptide #2 as compared to saline before exposure to SIN-I toxicity, Mutated peptide #2 failed to protect against SIN-I toxicity as shown. The presented experiment was repeated 3 times. *p<0.05, as compared to control cells exposed to the same toxic insult.

Figure 14:
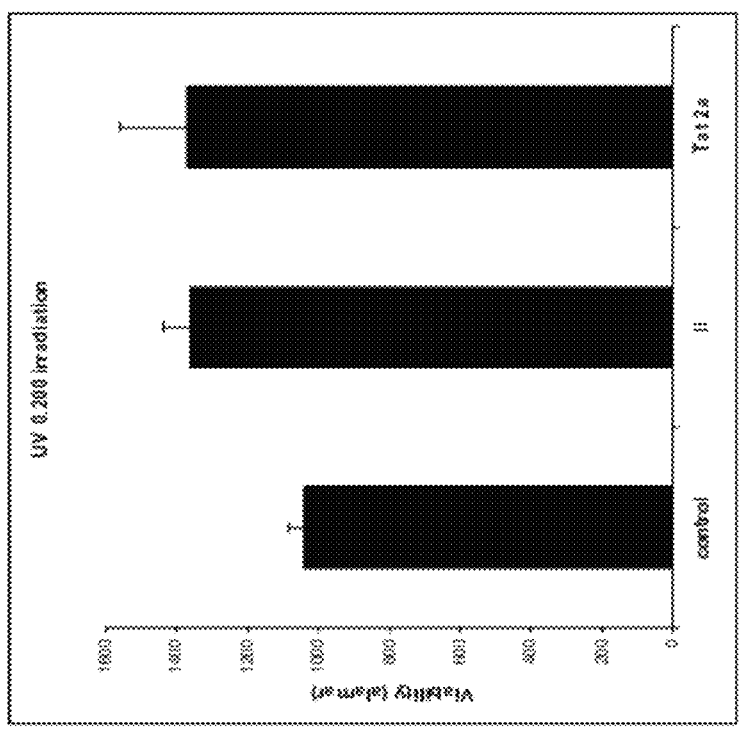

FIG. 14 is a bar graph illustrating that DJ-1-related peptides are protective in a cellular model against UV radiation. Increased metabolic activities were found when HaCaT cells were pretreated with DJ-1-related peptide II (SEQ ID NO: 8) or TAT 2a (SEQ ID NO:24) as compared to saline before exposure to UV radiation. The presented experiment was repeated 3 times. *p<0.05, as compared to control.

FIGS. 15A-B are bar graphs illustrating that intrastriatal TAT 2a peptide injection protects against in vivo 6-hydroxydopamine hemiparkinsonian mice model. 2 µl of 100 µM peptide TAT 2a (SEQ ID NO: 24) dissolved in saline or saline alone were injected stereotactically into the right striatum one hour before 6-hydroxydopamine lesioning. Significantly reduced amphetamine-induced rotations at 2 and 4-weeks after the lesioning was found in the peptide treated mice as compared to controls,*p<0.01 (FIG. 15A). Moreover, a smaller fraction of the lesioned mice rotated in response to amphetamine injection (FIG. 15B). The experiment was repeated twice.

Figure 16A:
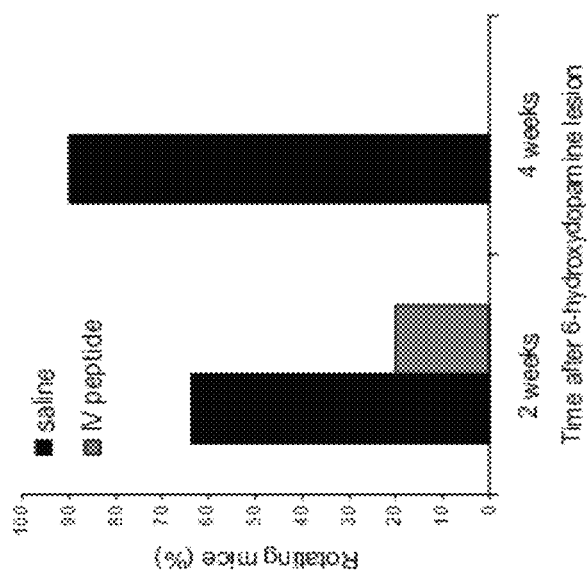
Figure 16B:
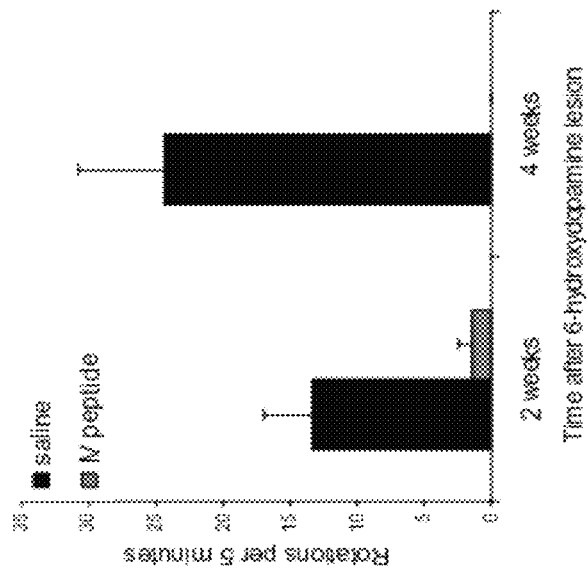

FIGS. 16A-B are bar graphs illustrating that intravenous (IV) peptide TAT 2a (SEQ ID NO: 24) injection protects against in vivo 6-hydroxydopamine hemiparkinsonian mice model. 50 µg peptide TAT 2a (SEQ ID NO: 24) or saline alone were injected IV 4 hours before 6-hydroxydopamine lesioning. Significantly reduced amphetamine-induced rotations were demonstrated in the IV peptide treated mice as compared to controls, *p<0.01 (FIG. 16A). A smaller fraction of the lesioned mice rotated in response to amphetamine injection (FIG. 16B).

Figure 17:
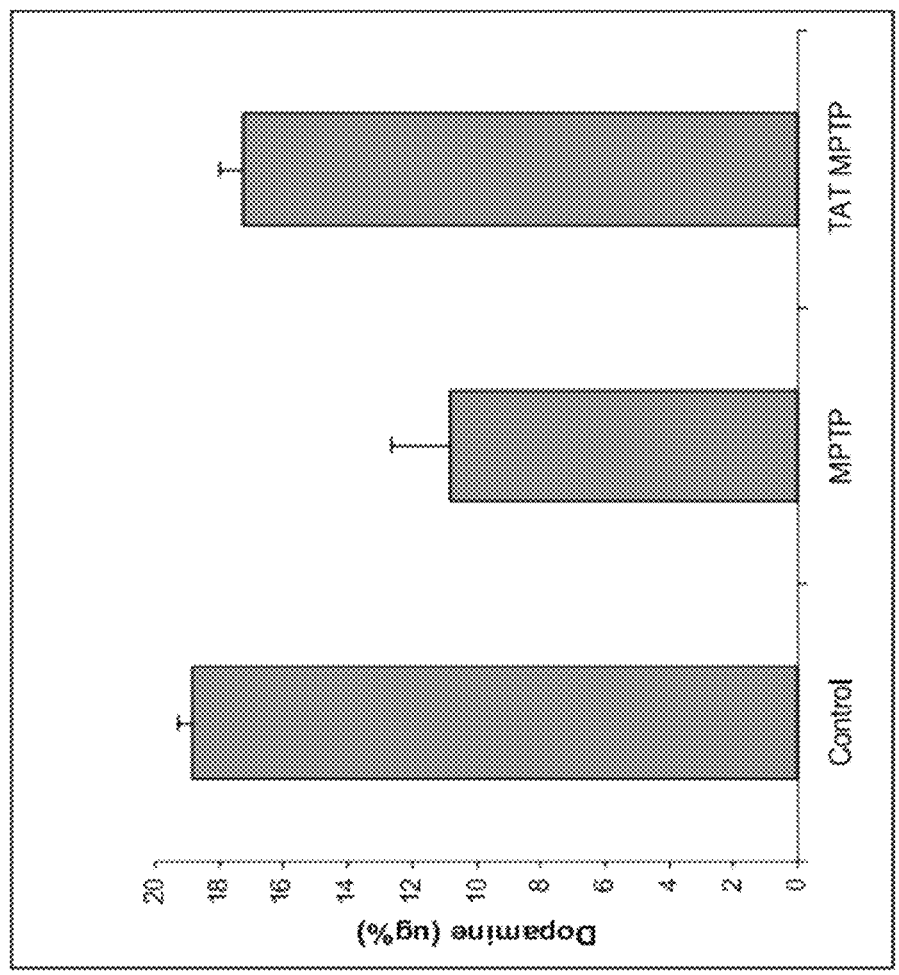

FIG. 17 is a bar graph illustrating that subcutaneous injection of peptide (SEQ ID NO: 25) protects against MPTP Parkinson's model.

DESCRIPTION OF SPECIFIC EMBODIMENTS OF THE INVENTION

Many neurodegenerative disorders are believed to be associated with oxidative stress such as Parkinson's disease and stroke. Accumulating data has revealed that DJ-1, a small 189 amino acid protein is involved various cellular processes, especially in oxidative stress and its use for the treatment of neurodegenerative diseases has been proposed.

The present disclosure, in some embodiments thereof, relates to DJ-1 related peptides that are useful for treating oxidative stress-related disorders. Two minimal core sequences on the DJ-1 protein have been identified in connection with the present disclosure which comprise therapeutic activity. A number of peptides have been prepared which included one or more of such core sequences and neuroprotecting properties have been demonstrated.

Specifically, it has been found that DJ-1 related peptides comprising at least one of the two core sequences are able to protect against toxic insults including 6-hydroxydopamine, dopamine and $H_2O_2$ in in vitro cell systems (FIGS. 1A-F, 2A-B, 3, 11, 12A), as well as serum depravation (FIG. 4A), whilst other DJ-1 related peptides which do not comprise either of the identified core sequences, comprise no such neuroprotective properties (FIG. 4B). The experiments were repeated in primary cultures (FIGS. 5A-B) and differentiated neural stem cells (FIG. 6) with the same results.

Another aspect of the present disclosure relates to an in vitro cell model of Parkinson's disorder which overexpresses mutant A53T alpha-synuclein in neuroblastoma cells. DJ-1 related peptides of embodiments of the present disclosure were demonstrated to be protective against 6-hydroxydopamine toxicity (FIG. 9) and $H_2O_2$ toxicity (FIG. 10) in the in vitro cell model.

Yet another aspect of the present disclosure relates to a cellular model for ALS and UV irradiation, in which DJ-1 related peptides of embodiments of the present disclosure were demonstrated to be protective in these assays as well (FIGS. 13 and 14).

Finally, DJ-1 related peptides of embodiments of the present disclosure are tested in an in vivo model of Parkinson's disease. Certain DJ-1 related peptides showed therapeutic activity following both local (FIGS. 15A-B) and systemic administration (FIGS. 16A-B).

Altogether, in accordance with the present disclosure, it has been found that peptides derived from DJ-1 ("DJ-1 related peptides) can be used for the treatment of oxidative stress related disorders. The phrase "oxidative stress conditions" as used herein, refers to conditions that elevate the level of reactive oxidative species (ROS) beyond the normal level. As mentioned this may result from a lack of antioxidants or from an over abundance free radicals. Exemplary ROS conditions include, but are not limited to 6-hydroxydopamine toxicity, hydrogen peroxide toxicity, UV radiation and dopamine toxicity.

In certain embodiments, certain aspects of the disclosure, as described in more full detail herein, relate to short DJ-1 related peptides no longer than 20 amino acids in length. More particularly, according to one aspect of the present disclosure, there is provided an isolated DJ-1 related peptide, or peptide mimetic thereof, no longer than 25 amino acids comprising at least 2 consecutive amino acids from the amino acid sequence as set forth in SEQ ID NO: 1, wherein the isolated peptide increases viability of a cell under oxidative stress conditions.

KGAEEMETVIPVDVMRRAGI—(SEQ ID NO: 1; also referred to herein as #peptide 2)

According to embodiments of this aspect of the present disclosure, the peptide comprises at least 3, 4, 5, 6, 7, 8, 9, 10, 11, 12, 13, 14, 15, 16, 17, 18, 19 or 20 consecutive amino acids from the amino acid sequence as set forth in SEQ ID NO: 1.

KGAEEMETVIPVDVMRRAGI—(SEQ ID NO: 1)

According to one embodiment of this aspect of the present disclosure, the peptide comprises no more than 10 consecutive amino acids of SEQ ID NO: 1.

According to other embodiments of this aspect of the present disclosure, the peptide comprises no more than 15 consecutive amino acids of SEQ ID NO: 1.

Exemplary sequences comprised in the peptide of this aspect of the present disclosure include SEQ ID NOs: 1-12, SEQ ID NO: 38 or SEQ ID NO: 39.

According to another aspect of the present disclosure, there is provided an isolated peptide, or peptide mimetic thereof, no longer than 25 amino acids comprising at least 2 consecutive amino acids from the amino acid sequence as set forth in SEQ ID NO: 2, wherein the isolated peptide increases viability of a cell under oxidative stress conditions.

EGPYDVVVLPGGNLGAQNLS—(SEQ ID NO: 2; also referred to herein as peptide #5)

According to embodiments of this aspect of the present disclosure, the peptide comprises at least 3, 4, 5, 6, 7, 8, 9, 10, 11, 12, 13, 14, 15, 16, 17, 18, 19 or 20 consecutive amino acids from the amino acid sequence as set forth in SEQ ID NO: 2.

According to one embodiment of this aspect of the present disclosure the peptide comprises no more than 10 consecutive amino acids of SEQ ID NO: 2.

According to other embodiments of this aspect of the present disclosure the peptide comprises no more than 15 consecutive amino acids of SEQ ID NO: 2.

Exemplary sequences comprised in the peptide of this aspect of the present disclosure include SEQ ID NOs: 2, 13-20, 40-42.

The term "peptide" as used herein refers to a polymer of natural or synthetic amino acids, encompassing native peptides (either degradation products, synthetically synthesized polypeptides or recombinant polypeptides) and peptidomimetics (typically, synthetically synthesized peptides), as well as peptoids and semipeptoids which are polypeptide analogs, which may have, for example, modifications rendering the peptides even more stable while in a body or more capable of penetrating into cells.

Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C.A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgin |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |

TABLE 2-continued

| Non-conventional amino acid | Code | Non-conventional amino acid | Code |
|---|---|---|---|
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |

TABLE 2-continued

| Non-conventional amino acid | Code | Non-conventional amino acid | Code |
|---|---|---|---|
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenylalanine | Mhphe |
| L-α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α ethylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine 1-carboxy-1-(2,2-diphenyl ethylamino)cyclopropane | Nnbhm Nmbc | N-(N-(3,3-diphenylpropyl) carbamylmethyl(1)glycine | Nnbhe |

The amino acids of the peptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having anti-bacterial properties.

As mentioned, the N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

These moieties can be cleaved in vivo, either by hydrolysis or enzymatically, inside the cell. Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —$NH_2$, —$NHR_2$ and —$NR_2R_3$) or ester (i.e. the hydroxyl group at the C-terminus is replaced with —$OR_2$). $R_2$ and $R_3$ are independently an aliphatic, substituted aliphatic, benzyl, substituted benzyl, aryl or a substituted aryl group. In addition, taken together with the nitrogen atom, $R_2$ and $R_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —$NH_2$, —$NHCH_3$, —$N(CH_3)_2$, —$NH(ethyl)$, —$N(ethyl)_2$, —$N(methyl)(ethyl)$, —$NH(benzyl)$, —$N(C1-C4\ alkyl)(benzyl)$, —$NH(phenyl)$, —$N(C1-C4\ alkyl)(phenyl)$, —$OCH_3$, —O-(ethyl), —O-(n-propyl), —O-(n-butyl), —O-(iso-propyl), —O-(sec-butyl), —O-(t-butyl), —O-benzyl and —O-phenyl.

The DJ-1 related peptides of the present invention may be attached (either covalently or non-covalently) to a penetrating agent.

As used herein the phrase "penetrating agent" refers to an agent which enhances translocation of any of the attached peptide across a cell membrane.

According to one embodiment, the penetrating agent is a peptide and is attached to the DJ-1 related peptide (either directly or non-directly) via a peptide bond.

Typically, peptide penetrating agents have an amino acid composition containing either a high relative abundance of positively charged amino acids such as lysine or arginine, or have sequences that contain an alternating pattern of polar/charged amino acids and non-polar, hydrophobic amino acids.

Examples of peptide penetrating agents include those set forth in SEQ ID NOs: 21-23. By way of non-limiting example, cell penetrating peptide (CPP) sequences may be used in order to enhance intracellular penetration. CPPs may included short and long versions of TAT (YGRKKRR—SEQ ID NO: 21 and YGRKKRRQRRR—SEQ ID NO: 22) and PTD (RRQRR—SEQ ID NO: 23). However, the disclosure is not so limited, and any suitable penetrating agent may be used, as known by those of skill in the art.

According to a particular embodiment, the peptides of the present invention are no longer than 25 amino acids (this includes the DJ-1 related peptide together with any additional attached sequence, such as a cell penetrating peptide as described above).

The peptides of the present invention may also comprise non-amino acid moieties, such as for example, hydrophobic moieties (various linear, branched, cyclic, polycyclic or heterocyclic hydrocarbons and hydrocarbon derivatives) attached to the peptides; non-peptide penetrating agents; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

The peptides of the invention may be linear or cyclic (cyclization may improve stability). Cyclization may take place by any means known in the art. Where the compound is composed predominantly of amino acids, cyclization may be via N- to C-terminal, N-terminal to side chain and N-terminal to backbone, C-terminal to side chain, C-terminal to backbone, side chain to backbone and side chain to side chain, as well as backbone to backbone cyclization. Cyclization of the peptide may also take place through non-amino acid organic moieties comprised in the peptide.

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Large scale peptide synthesis is described by Andersson Biopolymers 2000; 55(3):227-50.

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides of the present invention. To produce a peptide of the present invention using recombinant technology, a polynucleotide encoding the peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

In addition to being synthesizable in host cells, the peptides of the present invention can also be synthesized using in vitro expression systems. These methods are well known in the art and the components of the system are commercially available.

As mentioned, the peptides of the present invention may be used to treat oxidative-stress related disorders.

As used herein the phrase "oxidative stress" refers to an undesirable imbalance where oxidants outnumber antioxidants. This situation can arise if the rate of ROS production overwhelms existing antioxidant defenses. In such circumstances, a series of cellular responses can occur that can lead to an even greater increase in ROS production. Excessive ROS production and its otherwise ineffective regulation can be detrimental to cells and tissues, inducing cellular damage that ultimately can lead to cell death (apoptosis). Oxidative stress-associated damage also can cause undesirable changes to the structural and functional integrities of cells that can lead to the propagation of cells instead of apoptosis. Additionally, oxidatively-damaged cellular macromolecules can trigger immune responses that can lead to disease. See generally, D. G. Lindsay et al. (2002) Mol. Aspects of Med. 23:1-38, incorporated herein by reference.

It will be appreciated that oxidative stress may be responsible for initiating or otherwise causing disease. Alternatively, or additionally, the progression of the disease can be affected by any resultant oxidative stress.

Hence the phrase "oxidative stress related disease" as used herein, refers to a disease or medical condition (including syndromes) wherein the onset or progression thereof is promoted by oxidative stress. Since oxidative stress is believed to be responsible for the pathogenesis of many neurological, heart, malignant and age-associated diseases, the present invention contemplates all such diseases including for example, atherosclerosis, autoimmune diseases, cancer, cardiovascular disease, cataract, dementia, diabetes and diabetic vasculopathy, and neurodegenerative diseases.

Exemplary neurodegenerative diseases include, but are not limited to Parkinson's disease, Multiple Sclerosis, ALS, multi-system atrophy, Alzheimer's disease, stroke, progressive supranuclear palsy, fronto-temporal dementia with parkinsonism linked to chromosome 17 and Pick's disease.

The peptides of the present invention may be provided per se or as part of a pharmaceutical composition, where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the DJ-1 related peptides accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (DJ-1 related peptides) effective to prevent, alleviate or ameliorate symptoms of a disorder (e.g., Parkinson's Disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to brain or blood levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

DJ-1 Related Peptides:

Based on bioinformatic data and screening of DJ-1 protein several peptide sequences of 20 amino-acid based on DJ-1 may be selected. The peptide sequences that demonstrate neuroprotective properties are designed as peptides #2 and #5 and their sequences are as follows:

```
Peptide #2:   KGAEEMETVIPVDVMRRAGI   SEQ ID NO: 1

Peptide #5:   EGPYDVVVLPGGNLGAQNLS   SEQ ID NO: 2
```

Shorter peptide derivatives of Peptide #2 may be synthesized as follows:

```
KGAEEMETVIPVD;    (Pep2a; SEQ ID NO: 3

TVIPVDVMRRAGI;    (Pep2b; SEQ ID NO: 4)

EMETVIPVDVMRR;    (Pep2c; SEQ ID NO: 5)

KGAEEMETVIPVDVM;  (SEQ ID NO: 6)

METVIPVDVMRRAGI;  (SEQ ID NO: 7)

VDVMRRAGI;        (Pep II; SEQ ID NO: 8)

KGAEEMETVIPV;     (Pep short2a; SEQ ID NO: 9)

GAEEME;           (Pep I; SEQ ID NO: 10)

DVMRRAGI;         (Pep short II; SEQ ID NO: 11)

TVIPV;            (Pep III; SEQ ID NO: 37)

VIP.              (Pep IV; SEQ ID NO: 12)
```

Shorter peptide derivatives of Peptide #5 may be synthesized as follows:

```
DVVVLPGG;            (Pep V; SEQ ID NO: 13)

EGPYDVVVLPGGN;       (SEQ ID NO: 14)

VLPGGNLGAQNLS;       (SEQ ID NO: 15)

DVVVLPGGNLGAQ;       (SEQ ID NO: 16)

EGPYDVVVLPGGNLG;     (SEQ ID NO: 17)

VVVLPGGNLGAQNLS;     (SEQ ID NO: 18)

EGPYDVVVL;           (SEQ ID NO: 19)
and

GNLGAQNLS.           (SEQ ID NO: 20)
```

The peptides are introduced into the cells using PULSin method, using the manufacturer's instructions.

The peptides are then attached to cell penetrating peptide (CPP) sequences in order enhance intracellular penetration. CPPs used included short and long versions of TAT (YGRKKRR—SEQ ID NO: 21 and YGRKKRRQRRR—SEQ ID NO: 22) and PTD (RRQRR—SEQ ID NO: 23).

Peptide derivatives of peptide #2 (attached to cell penetrating peptides) are as follows:

```
                      SEQ ID NO: 24
Pep 2 TAT a:          YGRKKRRKGAEEMETVIPVD

SEQ ID NO: 25
Pep 2 TAT b:          YGRKKRRTVIPVDVMRRAGI

SEQ ID NO: 26
Pep 2 TAT c:          YGRKKRREMETVIPVDVMRR

SEQ ID NO: 27
Pep 2 PTD-5 a:        RRQRRKGAEEMETVIPVDVM

SEQ ID NO: 28
Pep 2 PTD-5 b:        RRQRRMETVIPVDVMRRAGI

SEQ ID NO: 29
Pep 2 nuc TAT:        YGRKKRRQRRRVDVMRRAGI
```

Peptide derivatives of peptide #5 (attached to cell penetrating peptides):

```
                      SEQ ID NO: 30
Pep5 TAT a:           YGRKKRREGPYDVVVLPGGN

SEQ ID NO: 31
Pep5 TAT b:           YGRKKRRVLPGGNLGAQNLS

SEQ ID NO: 32
Pep5 TAT c:           YGRKKRRDVVVLPGGNLGAQ

SEQ ID NO: 33
Pep 5 PTD-5 a:        RRQRREGPYDVVVLPGGNLG

SEQ ID NO: 34
Pep 5 PTD-5 b:        RRQRRVVVLPGGNLGAQNLS

SEQ ID NO: 35
Pep 5 nuc TAT a:      YGRKKRRQRRREGPYDVVVL

SEQ ID NO: 36
Pep 5 nuc TAT b:      YGRKKRRQRRRGNLGAQNLS
```

Cells:

Human neuroblastoma SH-SY5Y cells are obtained from the American tissue Type Culture Collection (ATCC, Rockville, USA). Cells are grown under sterile conditions as monolayer in DMEM medium supplemented with 10% heat-inactivated fetal calf serum (FCS), gentamicin (50 mg/ml), and glutamine (5 mM) in a 5% $CO_2$ humidified atmosphere at 37° C. The medium is routinely changed every 4 days, and cells are passaged every 8 days. All experiments are performed on cells which are near confluence.

The immortalized human HaCaT keratinocyte cells are used to test DJ-1 related peptides ability to protect against UV radiation induced injury. Cells are maintained in minimal essential medium containing 0.075 mM $Ca^{2+}$ (MEM-75) and 10% FCS in 5 cm Petri-dishes and subcultured every 3-4 days.

Primary Cultures and Neural Stem Cells:

Neural progenitor/stem cells are isolated from murine cortex of postnatal c57/bl mice and cultured as neurospheres. Neural and astroglial differentiation are induced.

Susceptibility of differentiated and undifferentiated neural progenitor/stem cells to oxidative and toxic insults are determined with and without prior pretreatment with DJ-1 related peptides.

Murine neuronal and astrocytes primary cultures derived from cortical tissues of post natal c57/bl mice are prepared and used in order to examine protective potential of DJ-1 related peptides.

Stable Cellular Transfections:

The coding region of human wild-type or A53T mutant alpha-synuclein cDNA is subcloned into pcDNA3.1-plasmid (BD Biosciences, Clontech). In order to achieve overexpression of A53T mutant alpha-synuclein, SH-SY5Y neuroblastoma cells are stably transfected with the plasmid containing A53T mutant alpha-synuclein. Transfections are performed using the lipofectamine 2000 reagent (Invitrogen, Carlsbad, Calif.). Selection of transfected cells is performed by treating the cells with lethal doses of geniticin (G-418). Naive neuroblastoma cells as well as cells stably transfected with the empty vector are used as controls.

Stable transfections are verified by measuring alpha-synuclein mRNA and protein levels using real-time PCR and Western blotting.

Treatments:

Neuroblastoma cells are contacted with hydrogen peroxide ($H_2O_2$) (0-1 mM; Sigma, Chemicals Co., St. Louis, Mo., USA), 6-hydroxydopamine (0-100 µM; Sigma, Chemicals Co., St. Louis, Mo., USA), dopamine (0-500 µM; Sigma, Chemicals Co., St. Louis, Mo., USA) and 3-(4-morpholinyl)-sydnonimine (SIN-I) (0-5 mM; Sigma), (which is a peroxynitrite free radical donor), in order to produce ROS formation.

Cell Toxicity and Viability Assays:

Several methods are used in order to determine the toxic effects of oxidative insults, neurotoxins and dopamine on cellular metabolic activity, mitochondrial activity and cell viability.

Alamar Blue:

Cells are seeded in 96-wells plates at the concentration of 5000 cells per well and allowed to attach over night. On the following day, the cells are exposed to increasing doses of dopamine (0-500 uM) for 4 hours in serum free medium. Alamar blue is a non toxic reagent which incorporates a redox indicator that changes color in response to metabolic activity. The reduction-induced colour change varies proportionately with cell number and time. A solution of 10% alamar blue is added in serum free medium 4 hours following exposure to increasing doses of dopamine, for 2 hours. Alamar blue fluorescence is measured by FLUOstar spectrofluorometer at the excitation wavelength of 544 nm and the emission wavelength of 590 nm. Each experiment is performed in triplicate for each treatment. The experiments are repeated 3 times.

Lactate Dehydrogenase (LDH) Cytotoxicity:

LDH released by damaged cells into the cell culture supernatant is determined using LDH cytotoxicity detection kit (Clontech laboratories, CA, USA), according to the manufacturer's instructions. The amount of LDH activity correlates to the number of damaged cells in the culture. LDH present in the culture supernatant participates in a coupled reaction converting a yellow tetrazolium salt into a red formazan product. The percentage of dead cells is calculated by the following formula of the absorbance values:

(triplicate absorbance−low control)/(maximum absorption−low control)×100.

Maximum absorption is obtained by treating the cells with 1% Triton X-100. The amount of enzyme activity is measured in a microplate reader by absorbance at 490 nm. Each experiment is done in triplicate for each treatment. The experiment is repeated 3 times.

Hoechst 33342:

In order to investigated changes in nuclear morphology of apoptotic cells, the cells are labeled with the nuclear stain Hoechst 33258 and examined under fluorescent microscopy. Hoechst 33342 is a cell fluorescent permeable dye with an affinity for DNA. Following toxin exposure, the cells are fixed with cold 70% ethanol, and incubated with Hoechst 33258 (10 ug/ml). Nuclear morphology is observed under a fluorescence microscope (Olympus, bx52, Leeds, Minneapolis, Minn.). Cells that exhibited reduced nuclear size, chromatin condensation, intense fluorescence, and nuclear fragmentation are considered to be apoptotic.

Hoechst 33342 enters cells with intact or damaged membranes and stains DNA in blue, thereby allowing evaluation of cell number in each well as well. A FLUOstar spectrofluorometer microplate reader may be used in order to evaluate the cell number in each well following exposure to different doses of various toxins. Excitation is performed at 346 nm and emission wavelength is determined at 460 nm. The experiment is performed in triplicate for each treatment. All experiments are repeated at least 3 times.

Western Blotting:

Over expression of WT and mutant alpha-synuclein is determined using Western blot. Cells are washed with PBS, trypsinated and collected by centrifugation. In order to prepare whole-cell lysate, the cells are re-suspended in a lysis buffer (containing 50 mM Tris-HCl, 0.1% SDS, 1% Triton X-100, 1 mM EDTA, 1% sodium-deoxycholate and a cocktail of protease inhibitors (Sigma)). Protein concentration are determined using a protein assay kit (Pierce). Twenty-five micrograms of total protein from each sample is separated by 12% SDS-PAGE gels and transferred to a nitrocellulose membrane. The membranes are blocked in 5% non-fat milk for 1 hour in room temperature and incubated overnight at 4° C. with monoclonal anti-alpha-synuclein antibody (LB509, 1:2000; Zymed Laboratories), followed by horseradish peroxidase conjugated secondary antibody (1:10000; Sigma) and developed with the ECL plus detection system (Amersham Pharmacia Biotech). The membranes are also incubated with mouse anti beta-actin antibodies (1:10000, Sigma), followed by horseradish peroxidase conjugated secondary antibody (1:10000; Sigma) and developed with the ECL plus detection system, in order to normalize the alpha-synuclein expression levels to beta-actin levels.

Immunocytochemistry for Alpha-Synuclein:

Cells were fixed with 4% paraformaldehyde and permeabilized with 0.5% Triton X-100. Subsequently, the fixed cells are incubated in a blocking solution followed by incubation overnight at 4° C. with monoclonal anti-alpha-synuclein antibody (LB509, 1:2000; Zymed Laboratories), followed by alexa-568 attached secondary antibodies. Nuclei are counterstained by DAPI (Sigma). The nuclear morphology is observed under a fluorescence microscope (Olympus, bx52, Leeds, Minneapolis, Minn.).

Evaluation of Apoptosis Rate by Immunocytochemistry:

Cells are fixed with 4% paraformaldehyde and permeabilized with 0.5% Triton X-100. Then the fixed cells are incubated in a blocking solution followed by incubation with Hoechst 33258 (10 ug/ml). The nuclear morphology is observed under a fluorescence microscope (Olympus, bx52, Leeds, Minneapolis, Minn.). Cells that exhibited reduced nuclear size, chromatin condensation, intense fluorescence, and nuclear fragmentation are considered to be apoptotic.

In Vivo 6-Hydroxydopamine Induced Hemiparkinsonian Mice Model:

Male c57/bl mice are used for this in vivo model of PD. The mice received a unilateral intrastriatal injection of 4 μg 6-hydroxydopamine hydrobromide (dissolved in 2 μl of saline containing 0.02% ascorbic acid) using a stereotaxic surgical procedure. Injections are targeted to the central striatum using the following coordinates: 0.7 mm anterior to bregma, 2.0 mm lateral to bregma, and 3.5 mm deep.

Behavioral effects of intrastriatal 6-hydroxydopamine lesioning are evaluated by accelerating rotarod examination and intrperitoneal amphetamine (2.5 mg/Kg)-induced rotational behaviour.

Measurements of catecholamine levels by high performance liquid chromatography (HPLC), and the degree of pathological damage, as evaluated by immunohistochemistry, are performed one month following the lesioning.

Statistical Analysis:

Statistical analysis is done using the SPSS software. Comparisons between two groups are conducted using a 2-tailed Student's t test. Statistical analyses among three or more groups are performed using analysis of variance (ANOVA) followed by least-significant difference (LSD) post hoc comparison. Results are presented by mean±standard deviation. Differences among groups are considered significant if the probability (p) of error was less than 5% ($p<0.05$).

Example 1

Analysis of Neuroprotective Activity of the Peptides of the Present Invention as Analyzed in Cell Lines Results Tat2A (SEQ ID NO: 24) is tested to determine its protective effect against neurotoxins, using an in vitro cellular platform. The peptides are delivered into neuroblastoma cells by the PULSin kit (Polyplus) and subsequently, by attachment to cell penetrating peptides. As illustrated in FIGS. 1A-F, some of the examined peptides showed significant protective effects against serum deprivation, oxidative and neurotoxic insults induced by exposure to hydrogen peroxide, 6-hydroxydopamine, and dopamine. These peptides reduced mitochondrial damage (evaluated by MTT assay), reduced metabolic damage (indicated by Alamar blue method), decreased cell toxicity (evaluated by LDH cytotoxicity detection kit, Clontech), and increased cell viability (by Hoechst staining).

DJ-1 mutated peptides did not show the protective effect of their corresponding non-mutated peptides as illustrated in FIGS. 2A-B which shows the protective effects of several DJ-1 related peptides (*$p<0.05$).

FIG. 3 illustrates that DJ-1-related peptides are protective in vitro against 6-hydroxydopamine toxicity, whereas FIG. 4A illustrates that DJ-1-related peptides are protective against serum deprivation.

Various non-conserved DJ-1 peptides were used as controls in order to verify the specific effect of the peptides of the present invention. Exposure of neuroblastoma cells to these peptides did not protect the cells from insults induced by 6-hydroxydopamine or hydrogen peroxide treatments, as illustrated in FIG. 4B.

Example 2

Analysis of Neuroprotective Activity of the Peptides of the Present Invention as Analyzed in Primary Murine Cultures Results T protective effects of DJ-1 peptides on primary cultures, and on differentiated and undifferentiated neural stem cells obtained from C57/bl mice brains were evaluated. Results show that the selected DJ-1 related peptides significantly protected against hydrogen peroxide and 6-hydroxydopamine toxicity. Specifically, FIGS. 5A-B illustrate protection of Tat 2A against oxidative and toxic injuries in primary mixed neuronal and astrocytes cultures from post natal mice brains. Neural progenitor/stem cells were isolated from murine cortex of postnatal c57/bl mice and cultured as neuro spheres. Neural and astroglial differentiation were induced.

Susceptibility of differentiated and undifferentiated neural progenitor/stem cells to oxidative and toxic insults was determined with and without prior pretreatment with DJ-1 related peptides, as illustrated in FIG. 6.

Example 3

Protection Against Mutant Alpha-Synuclein Toxicity

A53T mutant alpha-synuclein is one of the causes for genetically inherited Parkinson's Disease. Neuroblastoma cells overexpressing mutated alpha-synuclein were used as a cellular platform for Parkinson's Disease. In order to achieve overexpression of A53T mutant alpha-synuclein, SH-SY5Y neuroblastoma cells were stably transfected with the plasmid containing A53T mutant alpha-synuclein.

Verification of overexpression of alpha-synuclein was effected through immunocytochemical staining for alpha synuclein. FIG. 7A illustrates alpha-synuclein staining of naïve neuroblastoma cells, while FIG. 7B illustrates alpha-synuclein staining of A53T mutant alpha-synuclein transfected cells.

Quantification of alpha-synuclein protein was performed using Western blotting, as illustrated in FIG. 8.

DJ-1 related peptides were shown to be protective against 6-hydroxydopamine toxicity in neuroblastoma cells overexpressing mutant A53T alpha-synuclein (FIG. 9) and against pure oxidative insult induced by hydrogen peroxide ($H_2O_2$) exposure (FIG. 10).

Example 4

DJ-1 Related Peptides are Protective Against Dopamine Toxicity

Neuroblastoma SH-SY5Y cells were exposed to increasing doses of dopamine, with or without prior treatment with DJ-1 related peptides. Vulnerability to dopamine was statistically significantly attenuated by DJ-1 related peptides treatment, as illustrated in FIG. 11.

Example 5

Protection Against Cellular Models of Amyotrophic Lateral Sclerosis (ALS)

NSC-34 cells were used as a cellular model for ALS. Increasing doses of hydrogen peroxide and SIN-I, an NO donor, which are implicated in the pathogenesis of ALS were used. DJ-1 related peptides #2 showed protective effects against $H_2O_2$ and SIN-I toxicity in this cellular model of ALS, as illustrated in FIGS. 12A-B and 13.

Example 6

Ability of DJ-1 Related Peptides to Protect Against UV Radiation

Cultured keratinocytes were used to examine the ability of DJ-1 related peptides to protect against the damaging effects of UV radiation. Several DJ-1 related peptides showed significant protective effects against UV radiation induced cell death, as presented in FIG. 14.

Example 7

DJ-1 Related Peptides are Protective Against In Vivo Models of Parkinson's Disease Recent studies have shown that proteins attached to tat can penetrate and affect the brain after intravenous and intraperitoneal administration [Kim et al., 2010; Doeppner et al., 2010]. The present inventors attached peptide 2a, (of 13 amino acids) to tat and tested it in the well established 6-hydroxydopamine hemiparkinsonian mice model.

Next, the protective abilities of intrastriatal injected DJ-1-related peptides were tested. Two groups of male c57/bl mice received either 2 µl of 100 µM of TAT 2a DJ-1-related peptide (SEQ ID NO: 24) dissolved in saline or saline alone, injected stereotactically into the right striatum. One hour later, 4 µg of 6-hydroxydopamine was injected using the same coordinates. Behavioral studies included amphetamine-induced rotational behavior and accelerating rotarod examinations.

The effect of the DJ-1 related peptide in the 6-hydroxydopamine model was tested twice. A total of ten c57/bl male mice were used for the first experiment and 26 were used in the second experiment. In both, significantly reduced amphetamine-induced rotations in the peptide treated mice were found as compared to controls (p<0.01). This was confirmed twice in each of the 2 experiments: first, 2 weeks after the 6-hydroxydopamine striatal lesioning and subsequently, after 4 weeks, as illustrated in FIGS. 15A-B.

Accelerating Rotarod examination revealed a significant difference (p=0.02) between TAT 2a peptide (SEQ ID NO: 24)-treated mice and saline-treated controls. Immunohistochemical staining for tyrosine hydroxylase (TH) revealed that the 6-hydroxydopamine-induced loss of TH staining in the lesioned striatum was reversed by tat 2a DJ-1 related peptide (SEQ ID NO: 24).

Next, the effect of systemic administration of the DJ-1-related peptide was examined. Intravenous delivery of the peptide was performed as a mean to modulate 6-hydroxydopamine hemiparkinsonian mice model. 50 µg of the peptide was administered intravenously, 4 hours before 6-hydroxydopamine lesioning. Compared to controls, a dramatic decrease in amphetamine-induced rotations in the peptide treated mice at 2-weeks and 4-weeks after the lesioning was found (FIGS. 16A-B).

Example 8

In order to generate an animal model for Parkinson's disease, mice were treated with 1-methyl-4-phenyl-1,2,3,6-tetrahydropyridine (MPTP). 5 mice (C57/bl) were injected for 5 consecutive days with 20 mg/kg MPTP (i.p.) in the presence and absence of the DJ-1 related peptide (0.4 mM subcutaneous; SEQ ID NO: 25). 18 days later, the mice were sacrificed and the dopamine level, in the two hemispheres was measured by HPLC.

Results

The results of the experiment are demonstrated in FIG. 17.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating Parkinson's disease or Multiple Sclerosis in a subject in need thereof, the method comprising administering to the subject a therapeutically effective amount of a DJ-1 related peptide directly attached to a cell penetrating agent, wherein the amino acid sequence of said DJ-1-related peptide is as set forth in SEQ ID NO: 3, wherein when said cell penetrating agent is a peptide cell penetrating agent, the amino acid sequence of said peptide cell penetrating agent is selected from the group consisting of SEQ ID NOs: 21-23, thereby treating the Parkinson's disease or Multiple Sclerosis.

2. The method of claim 1, wherein said peptide cell penetrating agent consists of the amino acid sequence as set forth in SEQ ID NO: 21.

* * * * *

```
                           SEQUENCE LISTING

<160> NUMBER OF SEQ ID NOS: 42

<210> SEQ ID NO 1
  <211> LENGTH: 20
  <212> TYPE: PRT
  <213> ORGANISM: Artificial seqence
  <220> FEATURE:
  <223> OTHER INFORMATION: Synthetic peptide

<400> SEQUENCE: 1

Lys Gly Ala Glu Glu Met Glu Thr Val Ile Pro Val Asp Val Met Arg
  1               5                   10                  15

Arg Ala Gly Ile
              20

<210> SEQ ID NO 2
  <211> LENGTH: 20
  <212> TYPE: PRT
  <213> ORGANISM: Artificial seqence
  <220> FEATURE:
  <223> OTHER INFORMATION: Synthetic peptide

<400> SEQUENCE: 2

Glu Gly Pro Tyr Asp Val Val Val Leu Pro Gly Gly Asn Leu Gly Ala
  1               5                   10                  15

Gln Asn Leu Ser
              20

<210> SEQ ID NO 3
  <211> LENGTH: 13
  <212> TYPE: PRT
  <213> ORGANISM: Artificial seqence
  <220> FEATURE:
  <223> OTHER INFORMATION: Synthetic peptide

<400> SEQUENCE: 3

Lys Gly Ala Glu Glu Met Glu Thr Val Ile Pro Val Asp
  1               5                   10

<210> SEQ ID NO 4
  <211> LENGTH: 13
  <212> TYPE: PRT
  <213> ORGANISM: Artificial seqence
  <220> FEATURE:
  <223> OTHER INFORMATION: Synthetic peptide

<400> SEQUENCE: 4

Thr Val Ile Pro Val Asp Val Met Arg Arg Ala Gly Ile
```

```
1               5                   10
```

<210> SEQ ID NO 5
<211> LENGTH: 13
<212> TYPE: PRT
<213> ORGANISM: Artificial seqence
<220> FEATURE:
<223> OTHER INFORMATION: Synthetic peptide

<400> SEQUENCE: 5

```
Glu Met Glu Thr Val Ile Pro Val Asp Val Met Arg Arg
1               5                   10
```

<210> SEQ ID NO 6
<211> LENGTH: 15
<212> TYPE: PRT
<213> ORGANISM: Artificial seqence
<220> FEATURE:
<223> OTHER INFORMATION: Synthetic peptide

<400> SEQUENCE: 6

```
Lys Gly Ala Glu Glu Met Glu Thr Val Ile Pro Val Asp Val Met
1               5                   10                  15
```

<210> SEQ ID NO 7
<211> LENGTH: 15
<212> TYPE: PRT
<213> ORGANISM: Artificial seqence
<220> FEATURE:
<223> OTHER INFORMATION: Synthetic peptide

<400> SEQUENCE: 7

```
Met Glu Thr Val Ile Pro Val Asp Val Met Arg Arg Ala Gly Ile
1               5                   10                  15
```

<210> SEQ ID NO 8
<211> LENGTH: 9
<212> TYPE: PRT
<213> ORGANISM: Artificial seqence
<220> FEATURE:
<223> OTHER INFORMATION: Synthetic peptide

<400> SEQUENCE: 8

```
Val Asp Val Met Arg Arg Ala Gly Ile
1               5
```

<210> SEQ ID NO 9
<211> LENGTH: 12
<212> TYPE: PRT
<213> ORGANISM: Artificial seqence
<220> FEATURE:
<223> OTHER INFORMATION: Synthetic peptide

<400> SEQUENCE: 9

```
Lys Gly Ala Glu Glu Met Glu Thr Val Ile Pro Val
1               5                   10
```

<210> SEQ ID NO 10
<211> LENGTH: 6
<212> TYPE: PRT
<213> ORGANISM: Artificial seqence
<220> FEATURE:
<223> OTHER INFORMATION: Synthetic peptide

<400> SEQUENCE: 10

```
Gly Ala Glu Glu Met Glu
1               5
```

```
<210> SEQ ID NO 11
<211> LENGTH: 8
<212> TYPE: PRT
<213> ORGANISM: Artificial seqence
<220> FEATURE:
<223> OTHER INFORMATION: Synthetic peptide

<400> SEQUENCE: 11

Asp Val Met Arg Arg Ala Gly Ile
1               5

<210> SEQ ID NO 12
<211> LENGTH: 3
<212> TYPE: PRT
<213> ORGANISM: Artificial seqence
<220> FEATURE:
<223> OTHER INFORMATION: Synthetic peptide

<400> SEQUENCE: 12

Val Ile Pro
1

<210> SEQ ID NO 13
<211> LENGTH: 8
<212> TYPE: PRT
<213> ORGANISM: Artificial seqence
<220> FEATURE:
<223> OTHER INFORMATION: Synthetic peptide

<400> SEQUENCE: 13

Asp Val Val Val Leu Pro Gly Gly
1               5

<210> SEQ ID NO 14
<211> LENGTH: 13
<212> TYPE: PRT
<213> ORGANISM: Artificial seqence
<220> FEATURE:
<223> OTHER INFORMATION: Synthetic peptide

<400> SEQUENCE: 14

Glu Gly Pro Tyr Asp Val Val Leu Pro Gly Gly Asn
1               5                   10

<210> SEQ ID NO 15
<211> LENGTH: 13
<212> TYPE: PRT
<213> ORGANISM: Artificial seqence
<220> FEATURE:
<223> OTHER INFORMATION: Synthetic peptide

<400> SEQUENCE: 15

Val Leu Pro Gly Gly Asn Leu Gly Ala Gln Asn Leu Ser
1               5                   10

<210> SEQ ID NO 16
<211> LENGTH: 13
<212> TYPE: PRT
<213> ORGANISM: Artificial seqence
<220> FEATURE:
<223> OTHER INFORMATION: Synthetic peptide

<400> SEQUENCE: 16

Asp Val Val Val Leu Pro Gly Gly Asn Leu Gly Ala Gln
1               5                   10
```

<210> SEQ ID NO 17
<211> LENGTH: 15
<212> TYPE: PRT
<213> ORGANISM: Artificial seqence
<220> FEATURE:
<223> OTHER INFORMATION: Synthetic peptide

<400> SEQUENCE: 17

Glu Gly Pro Tyr Asp Val Val Val Leu Pro Gly Gly Asn Leu Gly
1               5                   10                  15

<210> SEQ ID NO 18
<211> LENGTH: 15
<212> TYPE: PRT
<213> ORGANISM: Artificial seqence
<220> FEATURE:
<223> OTHER INFORMATION: Synthetic peptide

<400> SEQUENCE: 18

Val Val Val Leu Pro Gly Gly Asn Leu Gly Ala Gln Asn Leu Ser
1               5                   10                  15

<210> SEQ ID NO 19
<211> LENGTH: 9
<212> TYPE: PRT
<213> ORGANISM: Artificial seqence
<220> FEATURE:
<223> OTHER INFORMATION: Synthetic peptide

<400> SEQUENCE: 19

Glu Gly Pro Tyr Asp Val Val Val Leu
1               5

<210> SEQ ID NO 20
<211> LENGTH: 9
<212> TYPE: PRT
<213> ORGANISM: Artificial seqence
<220> FEATURE:
<223> OTHER INFORMATION: Synthetic peptide

<400> SEQUENCE: 20

Gly Asn Leu Gly Ala Gln Asn Leu Ser
1               5

<210> SEQ ID NO 21
<211> LENGTH: 7
<212> TYPE: PRT
<213> ORGANISM: Artificial seqence
<220> FEATURE:
<223> OTHER INFORMATION: Synthetic peptide

<400> SEQUENCE: 21

Tyr Gly Arg Lys Lys Arg Arg
1               5

<210> SEQ ID NO 22
<211> LENGTH: 11
<212> TYPE: PRT
<213> ORGANISM: Artificial seqence
<220> FEATURE:
<223> OTHER INFORMATION: Synthetic peptide

<400> SEQUENCE: 22

Tyr Gly Arg Lys Lys Arg Arg Gln Arg Arg
1               5                   10

<210> SEQ ID NO 23
<211> LENGTH: 5
<212> TYPE: PRT
<213> ORGANISM: Artificial seqence
<220> FEATURE:
<223> OTHER INFORMATION: Synthetic peptide

<400> SEQUENCE: 23

Arg Arg Gln Arg Arg
1               5

<210> SEQ ID NO 24
<211> LENGTH: 20
<212> TYPE: PRT
<213> ORGANISM: Artificial seqence
<220> FEATURE:
<223> OTHER INFORMATION: Synthetic peptide

<400> SEQUENCE: 24

Tyr Gly Arg Lys Lys Arg Arg Lys Gly Ala Glu Glu Met Glu Thr Val
1               5                   10                  15

Ile Pro Val Asp
            20

<210> SEQ ID NO 25
<211> LENGTH: 20
<212> TYPE: PRT
<213> ORGANISM: Artificial seqence
<220> FEATURE:
<223> OTHER INFORMATION: Synthetic peptide

<400> SEQUENCE: 25

Tyr Gly Arg Lys Lys Arg Arg Thr Val Ile Pro Val Asp Val Met Arg
1               5                   10                  15

Arg Ala Gly Ile
            20

<210> SEQ ID NO 26
<211> LENGTH: 20
<212> TYPE: PRT
<213> ORGANISM: Artificial seqence
<220> FEATURE:
<223> OTHER INFORMATION: Synthetic peptide

<400> SEQUENCE: 26

Tyr Gly Arg Lys Lys Arg Arg Glu Met Glu Thr Val Ile Pro Val Asp
1               5                   10                  15

Val Met Arg Arg
            20

<210> SEQ ID NO 27
<211> LENGTH: 20
<212> TYPE: PRT
<213> ORGANISM: Artificial seqence
<220> FEATURE:
<223> OTHER INFORMATION: Synthetic peptide

<400> SEQUENCE: 27

Arg Arg Gln Arg Arg Lys Gly Ala Glu Glu Met Glu Thr Val Ile Pro
1               5                   10                  15

Val Asp Val Met
            20

<210> SEQ ID NO 28
<211> LENGTH: 20

```
<212> TYPE: PRT
<213> ORGANISM: Artificial seqence
<220> FEATURE:
<223> OTHER INFORMATION: Synthetic peptide

<400> SEQUENCE: 28

Arg Arg Gln Arg Arg Met Glu Thr Val Ile Pro Val Asp Val Met Arg
1               5                   10                  15

Arg Ala Gly Ile
            20

<210> SEQ ID NO 29
<211> LENGTH: 20
<212> TYPE: PRT
<213> ORGANISM: Artificial seqence
<220> FEATURE:
<223> OTHER INFORMATION: Synthetic peptide

<400> SEQUENCE: 29

Tyr Gly Arg Lys Lys Arg Arg Gln Arg Arg Val Asp Val Met Arg
1               5                   10                  15

Arg Ala Gly Ile
            20

<210> SEQ ID NO 30
<211> LENGTH: 20
<212> TYPE: PRT
<213> ORGANISM: Artificial seqence
<220> FEATURE:
<223> OTHER INFORMATION: Synthetic peptide

<400> SEQUENCE: 30

Tyr Gly Arg Lys Lys Arg Arg Glu Gly Pro Tyr Asp Val Val Val Leu
1               5                   10                  15

Pro Gly Gly Asn
            20

<210> SEQ ID NO 31
<211> LENGTH: 20
<212> TYPE: PRT
<213> ORGANISM: Artificial seqence
<220> FEATURE:
<223> OTHER INFORMATION: Synthetic peptide

<400> SEQUENCE: 31

Tyr Gly Arg Lys Lys Arg Arg Val Leu Pro Gly Gly Asn Leu Gly Ala
1               5                   10                  15

Gln Asn Leu Ser
            20

<210> SEQ ID NO 32
<211> LENGTH: 20
<212> TYPE: PRT
<213> ORGANISM: Artificial seqence
<220> FEATURE:
<223> OTHER INFORMATION: Synthetic peptide

<400> SEQUENCE: 32

Tyr Gly Arg Lys Lys Arg Arg Asp Val Val Val Leu Pro Gly Gly Asn
1               5                   10                  15

Leu Gly Ala Gln
            20

<210> SEQ ID NO 33
```

```
<211> LENGTH: 20
<212> TYPE: PRT
<213> ORGANISM: Artificial seqence
<220> FEATURE:
<223> OTHER INFORMATION: Synthetic peptide

<400> SEQUENCE: 33

Arg Arg Gln Arg Arg Glu Gly Pro Tyr Asp Val Val Val Leu Pro Gly
1               5                   10                  15

Gly Asn Leu Gly
            20

<210> SEQ ID NO 34
<211> LENGTH: 20
<212> TYPE: PRT
<213> ORGANISM: Artificial seqence
<220> FEATURE:
<223> OTHER INFORMATION: Synthetic peptide

<400> SEQUENCE: 34

Arg Arg Gln Arg Arg Val Val Val Leu Pro Gly Gly Asn Leu Gly Ala
1               5                   10                  15

Gln Asn Leu Ser
            20

<210> SEQ ID NO 35
<211> LENGTH: 20
<212> TYPE: PRT
<213> ORGANISM: Artificial seqence
<220> FEATURE:
<223> OTHER INFORMATION: Synthetic peptide

<400> SEQUENCE: 35

Tyr Gly Arg Lys Lys Arg Arg Gln Arg Arg Glu Gly Pro Tyr Asp
1               5                   10                  15

Val Val Val Leu
            20

<210> SEQ ID NO 36
<211> LENGTH: 20
<212> TYPE: PRT
<213> ORGANISM: Artificial seqence
<220> FEATURE:
<223> OTHER INFORMATION: Synthetic peptide

<400> SEQUENCE: 36

Tyr Gly Arg Lys Lys Arg Arg Gln Arg Arg Gly Asn Leu Gly Ala
1               5                   10                  15

Gln Asn Leu Ser
            20

<210> SEQ ID NO 37
<211> LENGTH: 5
<212> TYPE: PRT
<213> ORGANISM: Artificial seqence
<220> FEATURE:
<223> OTHER INFORMATION: Synthetic peptide

<400> SEQUENCE: 37

Thr Val Ile Pro Val
1               5

<210> SEQ ID NO 38
<211> LENGTH: 2
<212> TYPE: PRT
```

```
<213> ORGANISM: Artificial seqence
<220> FEATURE:
<223> OTHER INFORMATION: Synthetic peptide

<400> SEQUENCE: 38

Val Asp
1

<210> SEQ ID NO 39
<211> LENGTH: 6
<212> TYPE: PRT
<213> ORGANISM: Artificial seqence
<220> FEATURE:
<223> OTHER INFORMATION: Synthetic peptide

<400> SEQUENCE: 39

Thr Val Ile Pro Val Asp
1               5

<210> SEQ ID NO 40
<211> LENGTH: 2
<212> TYPE: PRT
<213> ORGANISM: Artificial seqence
<220> FEATURE:
<223> OTHER INFORMATION: Synthetic peptide

<400> SEQUENCE: 40

Val Leu
1

<210> SEQ ID NO 41
<211> LENGTH: 2
<212> TYPE: PRT
<213> ORGANISM: Artificial seqence
<220> FEATURE:
<223> OTHER INFORMATION: Synthetic peptide

<400> SEQUENCE: 41

Gly Asn
1

<210> SEQ ID NO 42
<211> LENGTH: 4
<212> TYPE: PRT
<213> ORGANISM: Artificial seqence
<220> FEATURE:
<223> OTHER INFORMATION: Synthetic peptide

<400> SEQUENCE: 42

Pro Gly Gly Asn
1
```